US006545157B1

(12) United States Patent
Morita et al.

(10) Patent No.: US 6,545,157 B1
(45) Date of Patent: Apr. 8, 2003

(54) DYE-FORMING METHOD, COLOR DEVELOPING COMPOSITIONS, PHOTOSENSITIVE MATERIALS AND COLOR DEVELOPING AGENT PRECURSORS

(75) Inventors: Kensuke Morita, Kanagawa (JP); Shun-ichi Ishikawa, Kanagawa (JP); Hideaki Naruse, Kanagawa (JP); Koki Nakamura, Kanagawa (JP); Toshio Kawagishi, Kanagawa (JP); Tadashi Ohmatsu, Kanagawa (JP); Kozo Aoki, Kanagawa (JP)

(73) Assignee: Fuji Photo Film Co., Ltd., Minami-Ashigara (JP)

( * ) Notice: Subject to any disclaimer, the term of this patent is extended or adjusted under 35 U.S.C. 154(b) by 0 days.

(21) Appl. No.: 09/987,360

(22) Filed: Nov. 14, 2001

Related U.S. Application Data

(62) Division of application No. 09/645,612, filed on Aug. 25, 2000, now Pat. No. 6,372,416.

(30) Foreign Application Priority Data

| | | |
|---|---|---|
| Aug. 26, 1999 | (JP) | 11-240595 |
| Aug. 26, 1999 | (JP) | 11-240596 |
| Aug. 26, 1999 | (JP) | 11-240597 |
| Sep. 28, 1999 | (JP) | 11-275336 |
| Sep. 30, 1999 | (JP) | 11-280206 |
| Nov. 12, 1999 | (JP) | 11-322912 |
| Mar. 9, 2000 | (JP) | 2000-65108 |
| Mar. 9, 2000 | (JP) | 2000-65110 |

(51) Int. Cl.$^7$ ..................................... C07D 211/06

(52) U.S. Cl. ................. 546/226; 546/268.4; 546/275.7; 548/324.1; 548/571; 430/350

(58) Field of Search ......................... 558/1, 2; 430/350; 546/268.4, 275.7, 226; 548/324.1, 571

(56) References Cited

U.S. PATENT DOCUMENTS

| | | | |
|---|---|---|---|
| 4,297,441 | A | 10/1981 | Kaneko et al. |
| 4,390,617 | A | 6/1983 | Okaniwa et al. |
| 4,409,321 | A | 10/1983 | Onodera et al. |
| 4,565,774 | A | 1/1986 | Kajiwara et al. |
| 5,583,255 | A | 12/1996 | Biavasco et al. |
| 6,013,420 | A | 1/2000 | Wingender et al. |
| 6,174,656 | B1 | 1/2001 | Nakamura et al. |

FOREIGN PATENT DOCUMENTS

| | | |
|---|---|---|
| JP | 11-167185 | 1/1999 |
| JP | 11-106361 | 4/1999 |

*Primary Examiner*—Joseph K. McKane
*Assistant Examiner*—Kamal Saeed
(74) *Attorney, Agent, or Firm*—Burns, Doane, Swecker & Mathis, LLP

(57) ABSTRACT

A dye-forming method comprising: reacting a dye-forming coupler and a color developing agent precursor represented by the following general formula (I):

(I)

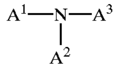

wherein $A^3$ represents a group other than a hydrogen atom which leaves, accompanied by the bonding electron pair with the nitrogen atom in general formula (I), to thereby form a color developing agent; $A^2$ represents a group which leaves in association with a dye-formation; and $A^1$ represents a group which forms a dye together with the nitrogen atom and the coupler.

2 Claims, No Drawings

DYE-FORMING METHOD, COLOR DEVELOPING COMPOSITIONS, PHOTOSENSITIVE MATERIALS AND COLOR DEVELOPING AGENT PRECURSORS

This application is a divisional of application Ser. No. 09/645,612, filed on Aug. 25, 2000, now U.S. Pat. No. 6,372,416.

FIELD OF THE INVENTION

This invention relates to novel color developing agent precursors, a dye-forming method, color developing compositions and photosensitive materials. More particularly, it relates to color developing agent precursors, a dye-forming method, color developing compositions and photosensitive materials which are useful in, for example, color printing materials for outputting digital image data.

DESCRIPTION OF THE RELATED ART

There have been widely employed photosensitive materials for obtaining images by forming dyes via coupling reactions. For example, conventional silver halide color photosensitive materials fall within this category of photosensitive materials for forming images with the use of coupling reactions. As an example of the methods for forming images on silver halide photosensitive materials, citation may be made of a method which involves the steps of incorporating a color developing agent and a colorless coupler into a material, oxidizing the color developing agent by using a silver halide in accordance with image data and coupling the obtained oxidant with the colorless coupler, thereby forming an image.

In the conventional silver halide photographic photosensitive materials, silver halides which oxidize color developing agents are needed in the formation of dyes. Silver halides, which oxidize relatively stable color developing agents contained in materials, are extremely strong oxidizing agents. Thus, it becomes difficult in some cases to contain such silver halides in a stable state together with couplers and surrounding media in materials. In addition, silver halides are expensive, which causes an increase in the production cost of silver halide photographic light-sensitive materials. Furthermore, the conventional image-forming method with the use of silver halide photographic light-sensitive materials usually involve complicated steps of development by using processing liquids, bleaching and fixing. Therefore, it is advantageous in view of cost and operation to employ a photosensitive material on which an image can be more conveniently formed without resort to any oxidizing agents. In recent years, there arises a strong demand for an image-forming method whereby full color digital image data can be economically and easily output. Therefore, it is profitable, if possible, to economically and easily form an image without using silver halides.

SUMMARY OF THE INVENTION

An object of the invention is to provide a method whereby a dye can be economically and easily formed without resort to any oxidizing agents such as silver halides; color developing compositions; and photosensitive materials using the same. Another object of the invention is to provide image-forming materials (in particular, image-forming materials for digital image data output) on which an image can be easily and economically formed without a need for liquid processing; and an image-forming method.

Other objects and effects of the present invention will become apparent from the following description.

The above-described objects of the present invention have been achieved by providing the following means.

(1) A dye-forming method comprising:

reacting a dye-forming coupler and a color developing agent precursor represented by the following general formula (I):

(I)

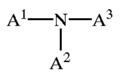

wherein $A^3$ represents a group other than a hydrogen atom which leaves, accompanied by the bonding electron pair with the nitrogen atom in general formula (I), to thereby form a color developing agent; $A^2$ represents a group which leaves in association with a dye-formation; and $A^1$ represents a group which forms a dye together with the nitrogen atom and the coupler.

(2) The dye-forming method according to the above (1), wherein said color developing agent precursor represented by general formula (I) is a compound represented by the following general formula (II):

(II)

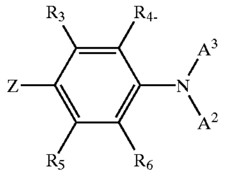

wherein Z represents —OH, —OPG or —$NR_1R_2$ (wherein PG represents a protective group; and $R_1$ and $R_2$ represent each an alkyl group or an aryl group); $R_3$, $R_4$, $R_5$ and $R_6$ represent each a hydrogen atom or a substituent; $A^3$represents a group which leaves from the nitrogen atom in general formula (II) accompanied by a bonding electron pair; and $A^2$ represents a group which leaves in association with the dye-formation; or $R_1$, $R_2$, $R_3$, $R_4$, $R_5$ and $R_6$ may be bonded to each other to form a ring in case of being possible.

(3) The dye-forming method according to the above (1), wherein the color developing agent precursor represented by general formula (I) is a compound represented by the following general formula (III):

(III)

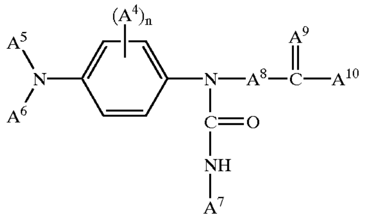

wherein $A^4$ represents a substituent; n is an integer of 0 to 4; $A^5$, $A^6$ and $A^7$ represent each a hydrogen atom or a substituent; $A^8$ represents a group represented by —O—, —S—, —N($A^{11}$)— or —C($A^{12}$) ($A^{13}$)— (wherein $A^{11}$ to $A^{13}$ represents each a substituent); $A^9$ represents a group represented by =O, =S, =N—$A^{14}$ or =C($A^{15}$)—C($A^{16}$)=N—$A^{17}$ (wherein $A^{14}$ to $A^{17}$ represents each a substituent); and $A^{10}$ represents a substituent.

(4) The dye-forming method according to the above (1), wherein group $A^2$ is a group which leaves in association with the dye-formation after the formation of a dye precursor via coupling between the color developing agent, which has been formed by the elimination of $A^3$, and the dye-forming coupler.

(5) The dye-forming method according to the above (2), wherein group $A^2$ is a group which leaves in association with the dye-formation after the formation of a dye precursor via coupling between the color developing agent, which has been formed by the elimination of $A^3$, and the dye-forming coupler.

(6) The dye-forming method according to the above (3), wherein group $A^2$ is a group which leaves in association with the dye-formation after the formation of a dye precursor via coupling between the color developing agent, which has been formed by the elimination of $A^3$, and the dye-forming coupler.

(7) The dye-forming method according to the above (1), wherein an activator or a precursor thereof, which is capable of acting on group $A^3$ in general formula (I) to thereby form a color developing agent, is further used.

(8) The dye-forming method according to the above (7), wherein said general formula (I) is represented by the following general formula (II):

(II)

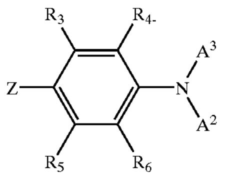

wherein Z represents —OH, —OPG or $—NR_1R_2$ (wherein PG represents a protective group; and $R_1$, and $R_2$ represent each an alkyl group or an aryl group); $R_3$, $R_4$, $R_5$ and $R_6$ represent each a hydrogen atom or a substituent; $A^3$ represents a group which leaves from the nitrogen atom in general formula (II) accompanied by a bonding electron pair; and $A^2$ represents a group which leaves in association with the dye-formation; or $R_1$, $R_2$, $R_3$, $R_4$, $R_5$ and $R_6$ may be bonded to each other to form a ring in case of being possible.

(9) The dye-forming method according to the above (7), wherein said general formula (I) is represented by the following general formula (III):

(III)

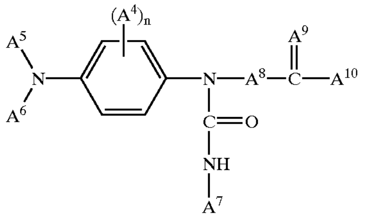

wherein $A^4$ represents a substituent; n is an integer of 0 to 4; $A^5$, $A^6$ and $A^7$ represent each a hydrogen atom or a substituent; $A^8$ represents a group represented by —O—, —S—, $—N(A^{11})—$ or $—C(A^{12})(A^{13})—$ (wherein $A^{11}$ to $A^{13}$ represents each a substituent); $A^9$ represents a group represented by =O, =S, $=N—A^{14}$ or $=C(A^{15})—C(A^{16})=N—A^{17}$ (wherein $A^{14}$ to $A^{17}$ represents each a substituent); and $A^{10}$ represents a substituent.

(10) The dye-forming method according to the above (7), wherein the activation effect of said activator is based on a nucleophilic substitution reaction or a nucleophilic addition reaction of $A^3$ with respect to an atom in the activator.

(11) The dye-forming method according to the above (7), wherein said activator contains a metal atom.

(12) A dye-forming method comprising forming a dye by reacting:

a precursor of an oxidation product of a p-phenylenediamine derivative or a p-aminophenol derivative;

an activator containing a metal atom which is capable of reacting with said precursor to thereby form an oxidation product of the p-phenylenediamine derivative or the p-aminophenol derivative; and a dye-forming coupler capable of undergoing a coupling reaction with said oxidant of the p-phenylenediamine derivative or the p-aminophenol derivative to thereby form a dye.

(13) A dye-forming method comprising forming a dye by reacting:

1) a color developing agent precursor represented by general formula (Ia):

(Ia)

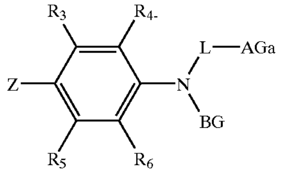

wherein Z represents a hydroxyl group or $—NR_1R_2$ (wherein $R_1$ and $R_2$ represent each an alkyl group or an aryl group); $R_3$, $R_4$, $R_5$ and $R_6$ represent each a hydrogen atom or a substituent; AGa represents a group which enables the compound of general formula (Ia) to interact with the compound of general formula (Q); L represents a group which leaves, as the result of said interaction, from the nitrogen atom in the compound of general formula (Ia) accompanied by the bonding electron pair; BG represents a blocking group which leaves in the course of the dye-formation; and $R_1$, $R_2$, $R_3$, $R_4$, $R_5$, and $R_6$ may be bonded to each other to form a ring in case of being possible;

2) an activator represented by general formula (Q):

$$(Aa)_m M^{n+} \quad (Q)$$

wherein M represents a metal atom having an electric charge n (wherein n is an integer of from 0 to 7); Aa represents an atomic group which neutralizes the electric charge of said metal ion; and m is an integer of from 0 to 7, provided that when n is 0, it is unnecessary that Aa neutralizes the electric charge of M and m is an integer of from 0 to 6, and when m is 2 or more, plurality of Aa may be either the same or different and may form a bonded structure together; and 3) a dye-forming coupler capable of reacting with an activated color developing agent, which is formed by the reaction between the compound represented by general formula (Ia) and the compound represented by general formula (Q) to thereby form a dye.

(14) The dye-forming method according to the above (11), wherein said metal atom is a copper, zinc or silver atom.

(15) The dye-forming method according to the above (7), wherein said activator contains a metal cation, and at least one compound selected from the group consisting of a halide anion, a carboxylic acid anion, a sulfonic acid anion, a sulfuric acidmonoester anion, a phosphoric acid diester anion, a β-ketoester anion, a β-diketone anion, an oxime anion, a hydroxamic acid anion, a tetraphenylboric acid anion, a phosphorus hexafluoride anion and a boron tetrafluoride anion.

(16) The dye-forming method according to the above (7), wherein said activator contains a meso-ion complex of a metal salt.

(17) The dye-forming method according to the above (16), wherein said meso-ion complex of a metal salt is a compound represented by the following general formula (IV):

$$(M^{n+})_p(A)_q(B)_r \qquad \text{(IV)}$$

wherein M represents a metal atom having a positive electric charge n; n is an integer of from 0 to 7; p is an integer of from 1 to 24; A represents an atomic group which has a negative electric charge of 1 to 7 and neutralizes the charge of the metal atom; q is an integer of from 0 to 24, provided that when q is 2 or more, plurality of A may be either the same or different and may form a bonded structure together; B represents an atomic group represented by general formula (V); r is an integer of from 1 to 24, provided that when r is 2 or more, plurality of B may be either the same or different and may form a bonded structure together; and the compound of formula (IV) may optionally have another atomic group bonded thereto which does not substantially neutralize the electric charges of other group:

(V)

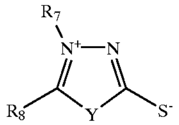

wherein Y represents O, S or N—$R_9$; $R_7$ and $R_9$ represent each a substituent; and $R_8$ represents a hydrogen atom or a substituent.

(18) The dye-forming method according to the above (17), wherein Y in general formula (V) represents N—$R_9$; $R_7$ and $R_9$ represent each an alkyl group, an aryl group or a heterocyclic group; and $R_8$ represents a hydrogen atom, an alkyl group, an aryl group or a heterocyclic group.

(19) The dye-forming method according to the above (16), wherein said color developing agent precursor is at least one member selected from p-phenylenediamine derivatives and p-aminophenol derivatives.

(20) The dye-forming method according to the above (16), wherein said color developing agent precursor is a compound represented by the following general formula (Ib):

(Ib)

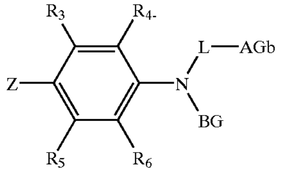

wherein Z represents —OH, —O(PG) or —$NR^1R^2$ (wherein PG represents a protective group; and $R^1$ and $R^2$ represent each an alkyl group or an aryl group); $R^3$, $R^4$, $R^5$ and $R^6$ represent each a hydrogen atom or a substituent; AGb represents a group which is capable of undergoing interaction with a meso-ion complex of a metal salt; L represents a group which leaves, as the result of said interaction, from the nitrogen atom in the compound of general formula (Ib) accompanied by the bonding electron pair; and BG represents a blocking group which leaves in the course of the dye-formation; or $R^1$, $R^2$, $R^3$, $R^4$, $R^5$ and $R^6$ may be bonded to each other to form a ring in case of being possible.

(21) A photosensitive material which contains:

a color developing agent precursor represented by general formula (I):

(I)

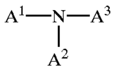

wherein $A^3$ represents a group other than a hydrogen atom which leaves, accompanied by the bonding electron pair with the nitrogen atom in general formula (I), to thereby form a color developing agent; $A^2$ represents a group which leaves in association with a dye-formation; and Al represents a group which forms a dye together with the nitrogen atom and the coupler;

a dye-forming coupler;

an activator capable of acting on group $A^3$ in general formula (I) to thereby form a color developing agent;

a polymerizable compound; and a photopolymerization initiator, provided that said polymerizable compound may be the same molecule as said color developing agent precursor, dye-forming coupler or activator.

(22) The photosensitive material according to the above (21), wherein general formula (I) is represented by general formula (II):

(II)

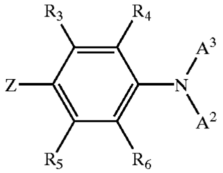

wherein Z represents —OH, —OPG or —$NR_1R_2$ (wherein PG represents a protective group; and $R_1$ and $R_2$ represent each an alkyl group or an aryl group); $R_3$, $R_4$, $R_5$, and $R_6$ represent each a hydrogen atom or a substituent; $A^3$ represents a group which leaves from the nitrogen atom in general formula (II) accompanied by a bonding electron pair; and $A^2$ represents a group which leaves in association with the dye-formation; or $R_1$, $R_2$, $R_3$, $R_4$, $R_5$ and $R_6$ may be bonded to each other to form a ring in case of being possible.

(23) The photosensitive material according to the above (21), wherein general formula (I) is represented by general formula (III):

(III)

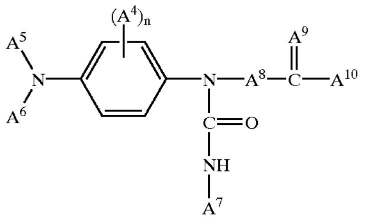

wherein $A^4$ represents a substituent; n is an integer of 0 to 4; $A^5$, $A^6$ and $A^7$ represent each a hydrogen atom or a substituent; $A^8$ represents a group represented by —O—, —S—, —N($A^{11}$)— or —C ($A^{12}$) ($A^{13}$)— (wherein $A^{11}$ to $A^{13}$ represents each a substituent); $A^9$ represents a group represented by =O, =S, =N—$A^{14}$ or =C($A^{15}$)—C($A^{16}$) =N—$A^{17}$ (wherein $A^{14}$ to $A^{17}$ represents each a substituent); and $A^{10}$ represents a substituent.

(24) The photosensitive material according to the above (21), wherein the activation effect of said activator is based on a nucleophilic substitution reaction or a nucleophilic addition reaction of $A^3$with respect to an atom in the activator.

(25) The photosensitive material according to the above (21), wherein said activator contains a metal atom.

(26) A photosensitive material which contains:

a precursor of an oxidation product of a p-phenylenediamine derivative or a p-aminophenol derivative, as a color developing agent precursor;

an activator containing a metal atom which is capable of reacting with said color developing agent precursor to thereby form the oxidation product of the p-phenylenediamine derivative or the p-aminophenol derivative;

a dye-forming coupler capable of undergoing a coupling reaction with said oxidation product of the p-phenylenediamine derivative or the p-aminophenol derivative to thereby form a dye;

a polymerizable monomer; and a photopolymerization initiator, provided that said polymerizable monomer may be the same molecule as said color developing agent precursor, activator or dye-forming coupler.

(27) A photosensitive material which contains:

a color developing agent precursor represented by general formula (Ia):

(Ia)

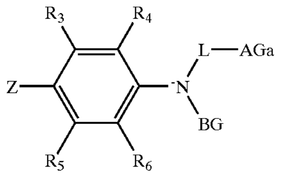

wherein Z represents a hydroxyl group or —$NR_1R_2$ (wherein $R_1$ and $R_2$ represent each an alkyl group or an aryl group); $R_3$, $R_4$, $R_5$ and $R_6$ represent each a hydrogen atom or a substituent; AGa represents a group which enables the compound of general formula (Ia) to interact with the compound of general formula (Q); L represents a group which leaves, as the result of said interaction, from the nitrogen atom in the compound of general formula (Ia) accompanied by the bonding electron pair; BG represents a blocking group which leaves in the course of the dye-formation; and $R_1$, $R_2$, $R_3$, $R_4$, $R_5$ and $R_6$ may be bonded to each other to form a ring in case of being possible;

an activator represented by general formula (Q):

$$(Aa)_m M^{n+} \quad (Q)$$

wherein M represents a metal atom having an electric charge n (wherein n is an integer of from 0 to 7); Aa represents an atomic group which neutralizes the electric charge of said metal ion; and m is an integer of from 0 to 7, provided that when n is 0, it is unnecessary that Aa neutralizes the electric charge of M and m is an integer of from 0 to 6, and when m is 2 or more, plurality of Aa may be either the same or different and may form a bonded structure together;

a dye-forming coupler capable of reacting with an activated color developing agent, which is formed by the reaction between the compound represented by general formula (Ia) with the compound represented by general formula (Q) to thereby form a dye;

a polymerizable monomer; and a photopolymerization initiator, provided that said polymerizable monomer may be the same molecule as said color developing agent precursor, activator or dye-forming coupler.

(28) The photosensitive material according to the above (25), wherein said metal atom is a copper, zinc or silver atom.

(29) The photosensitive material according to the above (21), wherein said activator contains a metal cation, and at least one compound selected from the group consisting of a halide anion, a carboxylic acid anion, a sulfonic acid anion, a sulfuric acid monoester anion, a phosphoric acid diester anion, a β-ketoester anion, a β-diketone anion, an oxime anion, a hydroxamic acid anion, a tetraphenylboric acid anion, a phosphorus hexafluoride anion and a boron tetrafluoride anion.

(30) The photosensitive material according to the above (21), wherein said activator contains a meso-ion complex of a metal salt.

(31) The photosensitive material according to the above (30), wherein said meso-ion complex of a metal salt is a compound represented by the following general formula (IV):

$$(M^{n+})_p(A)_q(B)_r \quad (IV)$$

wherein M represents a metal atom having a positive electric charge n; n is an integer of from 0 to 7; p is an integer of from 1 to 24; A represents an atomic group which has a negative electric charge of 1 to 7 and neutralizes the charge of the metal atom; q is an integer of from 0 to 24, provided that when q is 2 or more, plurality of A may be either the same or different and may form a bonded structure together; B represents an atomic group represented by general formula (V); r is an integer of from 1 to 24, provided that when r is 2 or more, plurality of B may be either the same or different and may form a bonded structure together; and the compound of formula (IV) may optionally have another atomic group bonded thereto which does not substantially neutralize the electric charges of other group:

(V)

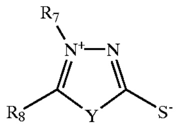

wherein Y represents O, S or N—$R_9$; $R_7$ and $R_9$ represent each a substituent; and $R_8$ represents a hydrogen atom or a substituent.

(32) The photosensitive material according to the above (31), wherein Y in general formula (V) represents N—$R_9$; $R_7$ and $R_9$ represent each an alkyl group, an aryl group or a heterocyclic group; and $R_8$ represents a hydrogen atom, an alkyl group, an aryl group or a heterocyclic group.

(33) A compound represented by the following general formula (VI):

(VI)

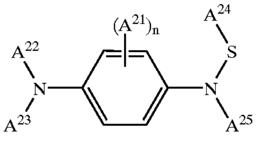

wherein $A^{21}$ and $A^{24}$ represent each a substituent; n is an integer of from 0 to 4; $A^{22}$ and $A^{23}$ represent each an alkyl group; and $A^{25}$ represents —C (═O)—$A^{26}$ or —$SO_2$—$A^{27}$ (wherein $A^{26}$ and $A^{27}$ represent each a substituent).

(34) The compound according to the above (33), wherein $A^{24}$ is represented by general formula (VII) and $A^{25}$ is represented by general formula (VIII):

(VII)

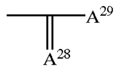

(VIII)

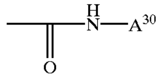

wherein $A^{28}$ represents ═O, ═S or ═N—$A^{31}$ (wherein $A^{31}$ represents a substituent); and $A^{29}$ and $A^{30}$ represent each a hydrogen atom or a substituent.

(35) A color developing composition which contains a color developing agent precursor represented by general formula (I) and a dye-forming coupler.

(36) The color developing composition according to the above (35), wherein the color developing agent precursor represented by general formula (I) is a compound represented by general formula (II).

(37) The color developing composition according to the above (35), wherein the color developing agent precursor represented by general formula (I) is a compound represented by general formula (III).

DETAILED DESCRIPTION OF THE INVENTION

Color Developing Agent Precursor

Examples of the color developing agent precursor of the invention include compounds prepared by capturing oxidants of color developing agents, which are usable in silver halide photographic photosensitive materials, by chemical species other than couplers (hereinafter, these chemical species will be called "capturers"). In this case, the capturer moiety in the color developing agent precursor is activated in the course of the dye-formation and an interchange between the capturer and the coupler takes place, thereby forming a dye.

It is favorable that the color developing agent precursor, which is particularly represented by general formula (I), is at least one member selected from among p-phenylenediamine derivatives and p-aminophenol derivatives. It is favorable that the p-phenylenediamine derivative or the p-aminophenol derivative is a compound having a moiety which is activated by an activator and leaves to thereby convert the derivative into an oxidant.

Preferable examples of the color developing agent precursor are compounds represented by the following general formula (II).

(II)

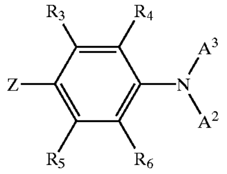

In general formula (II), Z represents —OH, —O(PG) or —$NR_1R_2$ wherein PG represents a protective group. As this protective group, use may be made of common ones.

$R_1$ and $R_2$ represent each an alkyl group or an aryl group or $R_1$ and $R_2$ may be bonded to each other to form a heterocyclic group. The alkyl groups represented by $R_1$ and $R_2$ include both of substituted alkyl groups and unsubstituted alkyl groups. These alkyl groups may be either branched or linear. When $R_1$ and $R_2$ represent each a substituted alkyl group, examples of the substituent include a cyano group, a sulfonylamino group, an acyl group, a hydroxyl group, an acylamino group, an acyloxy group, halogen atoms and alkyloxycarbonyl groups. These substituents may be further substituted by, for example, an alkyl group or an aryl group. Particular examples of the alkyl groups include methyl group, ethyl group, propyl group, dodoecyl group, 2-hydroxyethyl group,2-cyanoethyl group, cyanomethyl group, 2-methoxyethyl group, 2-ethoxycarbonyl group and 2-(methylsulfonylamino)ethyl group.

The aryl groups represented by $R_1$ and $R_2$, include both of substituted aryl groups and unsubstituted aryl groups. These aryl groups may have either a monocyclic structure or a fused ring structure composed of two or more rings fused together. When $R_1$, and $R_2$, represent each a substituted aryl group, examples of the substituent include those which will be cited hereinafter as examples of substituents represented by $R^3$ to $R^6$. These substituents may be further substituted by, for example, an alkyl group or an aryl group. Particular examples of the aryl groups include phenyl group and naphthyl group.

Alternatively, $R_1$ and $R_2$ may be bonded together to form a heterocyclic group. The heterocyclic group may be either a substituted group or an unsubstituted group. As the heterocyclic group, 5-, 6- or 7-membered heterocyclic group is favorable. The heterocyclic groups may have either a monocyclic structure or a fused ring structure composed of two or more rings fused together. As the hetero atom involved in the heterocyclic group, a nitrogen atom, an oxygen atom or a sulfur atom is favorable.

In general formula (I) as given above, $R_3$, $R_4$, $R_5$, and $R_6$ represent each a hydrogen atom or a substituent.

Preferable examples of the substituents represented respectively by $R_3$, $R_4$, $R_5$ and $R_6$ include halogen atoms (for example, chloro, bromo), alkyl groups (for example, methyl, ethyl, isopropyl, n-butyl, t-butyl), aryl groups (for example, phenyl, tolyl, xylyl), heterocyclic groups (for example, 2-pyridyl, N-pyrrolidinyl), carbonamido groups (for example, acetylamino, propionylamino, butyroylamino, benzoylamino), sulfonamido groups (for example, methanosulfonylamino, ethanesulfonylamino, benzenesulfonylamino, toluenesulfonylamino), alkoxy groups (for example, methoxy, ethoxy), aryloxy groups (for example, phenoxy), alkylthio groups (for example, methylthio, ethylthio, butylthio), arylthio groups (for example, phenylthio, tolylthio), amino groups (for example, methylamino, phenylamino), carbamoyl groups (for example, methylcarbamoyl, dimethylcarbamoyl, ethylcarbamoyl, diethylcarbamoyl, dibutylcarbamoyl, piperidinocarbamoyl, morpholinocarbamoyl, phenylcarbamoyl, methylphenylcarbamoyl, ethylphenylcarbamoyl, benzylphenylcarbamoyl), sulfamoyl groups (for example, methylsulfamoyl, dimethylsulfamoyl, ethylsulfamoyl, diethylsulfamoyl, dibutylsulfamoyl, piperidinosulfamoyl, morpholinosulfamoyl, phenylsulfamoyl, mehtylphenylsulfamoyl, ethylphenylsulfamoyl, benzylphenylsulfamoyl), cyano group, sulfonyl groups (for example, methanesulfonyl, ethanesulfonyl, phenylsulfonyl, 4-chlorophenylsulfonyl, p-toluenesulfonyl), alkoxycarbonyl groups (for example, methoxycarbonyl, ethoxycarbonyl, butoxycarbonyl), aryloxycarbonyl groups (for example, phenoxycarbonyl), acyl groups (for example, acetyl, propionyl, butyroyl, benzoyl, alkylbenzoyl), ureido groups (for example, methylaminocarbonamido, diethylaminocarbonamido), urethane groups (for example, methoxycarbonamido, butoxycarbonamido) and acyloxy groups (for example, acetyloxy, propionyloxy, butyroyloxy).

$R_1$ and $R_3$, $R_1$ and $R_5$, $R_2$ and $R_3$, and $R_2$ and $R_5$ may be each bonded together to form a heterocycle, preferably a 5- to 7-membered heterocycle. It is also possible that $R_3$ and $R_4$, and $R_5$ and $R_3$ are each bonded together to form a ring. In this case, the rings may be either heterocycles or homocylces. Moreover, each of these cycles may be saturated, partly saturated or incompletely saturated and preferably have from 5 to 7 members.

$A_3$ represents a moiety corresponding to the capturer as described above. Namely, $A^3$ represents a group which leaves under the action of heat or an activator. In case of leaving under the action of an activator, $A^3$ has an atomic group capable of undergoing interaction with the activator. Examples of the atomic group capable of undergoing the interaction with an activator include carboxyl groups, thiocarbonyl groups, selenocarbonyl groups, tellurocarbonyl groups, thioether groups, selenoether groups, amino groups, ether groups, hydroxy groups (including enol, phenol), carboamido groups, polyether groups, crown ether groups, azo groups, hydroxyimino groups, imino groups, carbonyl groups and heterocyclic groups having a nitrogen atom or a sulfur atom in the ring. Among all, carboxyl groups, thiocarbonyl groups, thioether groups, amino groups, hydroxy groups (including enol, phenol), polyether groups, crown ether groups, hydroxyimino groups, imino groups and heterocyclic groups having a nitrogen atom or a sulfur atom in the ring are preferable and carboxyl groups, thiocarbonyl groups, amino groups, hydroxyimino groups and heterocyclic groups having a nitrogen atom or a sulfur atom in the ring are still preferable. It is also preferable to use atomic groups composed of these groups combined together.

Preferable examples of $A^3$ are groups having a partial structure represented by the following general formula (IX).

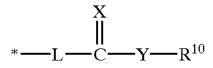

(IX)

In general formula (IX), "★" stands for a moiety bonded to the nitrogen atom.

In general formula (IX), X represents a sulfur atom, a selenium atom, an =NOH group or an $=NR^{11}$ group.

In general formula (IX), Y represents a sulfur atom, an oxygen atom, $-N(R^{12})-$ or $-C(R^{13})(R^{14})-$. It is preferable that Y is a sulfur atom, an oxygen atom or $-N(R^{12})-$.

In general formula (IX), $R^{10}$ represents an alkyl group, an aryl group or a heterocyclic group, and $R^{11}$, $R^{12}$, $R^{13}$ and $R^{14}$ represent each an alkyl group, an aryl group or a heterocyclic group. Examples of these alkyl and aryl groups include those cited above as examples of the groups represented by $R^3$ to $R^6$. Examples of the heterocyclic groups include those cited above as examples of the groups formed by bonding $R^1$ and $R^3$ to each other. $R^{10}$ and $R^{11}$, $R^{10}$ and $R^{12}$, $R^{10}$ and $R^{13}$, $R^{10}$ and $R^{14}$ and $R^{13}$ and $R^{14}$ may be each bonded together to form a ring, preferably a 5- to 7-membered ring.

In general formula (IX), L represents a group which leaves, as the result of heating or interaction with an activator, from the nitrogen atom in general formula (I) accompanied with a bonding electron pair. It is preferable that Lisa sulfur atom, $-N(R^{15})-$ or $-C(R^{16})(R^{17})-$. $R^{15}$ represents an alkyl group, an aryl group, a heterocyclic group or a bond. Examples of these alkyl and aryl groups include those cited above as examples of the groups represented by $R^3$ to $R^6$. Examples of the heterocyclic groups include those cited above as examples of the groups formed by bonding $R^1$ and $R^3$ to each other. At least one of $R^{15}$, $R^{16}$ and $R^{17}$ may be bonded to $-C(=X)-Y-R^{10}$ to form a ring, which is preferably a 5- to 7-membered ring. $R^{16}$ and $R^{17}$ represent each an alkyl group, an aryl group, a heterocyclic group, a cyano group, a trifluoromethyl group, a sulfonyl group, a carbamoyl group, a halogen atom, an amido group, a sulfamoyl group, an acyl group or a bond. Examples of these groups include those cited above as examples of the groups represented by $R^3$ to $R^6$. Examples of the heterocyclic groups include those cited above as examples of the groups formed by bonding $R^1$ and $R^3$ to each other. $R^{16}$ and $R^{17}$, $R^{18}$ and $-C(=X)-Y-R^{10}$, and $R^{17}$ and $-C(=X)-Y-R^{10}$ may be each bonded together to form a ring, which is preferably a 5- to 7-membered ring. It is favorable that at least one of $R^{16}$ and $R^{17}$ is a group having a Hammett sigma-para (δp) constant of +0.3 or more (for example, cyano, trifluoromethyl, sulfonyl, carbamoyl, sulfamoyl, acyl).

In general formula (II), $A^2$ represents a protective group which leaves in the course of the dye-formation. It is preferable that $A^2$ also has a function of stabilizing the compound represented by general formula (II). From this viewpoint, an electrophilic group is preferable therefor. Among all, it is preferable that $A^2$ is a group represented by the following general formula (X).

$$★★-W-R^{18} \qquad (X)$$

In general formula (X), "★★" represents a moiety bonded to the nitrogen atom in general formula (II).

In general formula (X), W represents an electrophilic divalent group. It is particularly preferable that W represents —$SO_2$—, —$CON(R^{19})$—, —COO— or —$SO_2N(R^{19})$— and —$CON(R^{19})$— is the most desirable. $R^{19}$ represents a hydrogen atom, an alkyl group or an aryl group. Among all, it is preferable that $R^{19}$ is a hydrogen atom.

In general formula (X), $R^{18}$ represents a hydrogen atom, an alkyl group, an aryl group, a heterocyclic group or an alkoxy group. Among all, it is preferable that $R^{18}$ represents an alkyl group or an aryl group and an alkyl group is the most desirable. Examples of these alkyl and aryl groups include those cited above as examples of the groups represented by $R^3$ to $R^6$.

In general formulae (Ia) and (Ib), $R_4$ to $R_6$ are as defined in general formula (II). L-AGa and L-AGb correspond to $A^3$ in general formula (II) while BG corresponds to $A^2$ in general formula (II) and examples thereof are also the same as described with respect to $A^3$ and $A^2$.

Examples of $A^4$ in general formula (III) include halogen atoms (for example, chloro, bromo), alkyl groups (for example, methyl, ethyl, isopropyl, n-butyl, t-butyl), aryl groups (for example, phenyl, tolyl, xylyl), heterocyclic groups (for example, 2-pyridyl, N-pyrrolidinyl), carbonamido groups (for example, acetylamino, propionylamino, butyroylamino, benzoylamino), sulfonamido groups (for example, methanosulfonylamino, ethanesulfonylamino, benzenesulfonylamino, toluenesulfonylamino), alkoxy groups (for example, methoxy, ethoxy), aryloxy groups (for example, phenoxy), alkylthio groups (for example, methylthio, ethylthio, butylthio), arylthio groups (for example, phenylthio, tolylthio), amino groups (for example, unsubstituted amino, amino substituted by aliphatic or aromatic groups such as methylamino, phenylamino), carbamoyl groups (for example, carbamoyl substituted by aliphatic, aromatic or heterocyclic groups and carbamoyl having a ring formed by the linkage of nitrogen atoms, such as methylcarbamoyl, dimethylcarbamoyl, ethylcarbamoyl, diethylcarbamoyl, dibutylcarbamoyl, piperidinocarbamoyl, morpholinocarbamoyl, phenylcarbamoyl, methylphenylcarbamoyl, ethylphenylcarbamoyl, benzylphenylcarbamoyl), sulfamoyl groups (for example, sulfamoyl substituted by aliphatic, aromatic or heterocyclic groups-and sulfamoyl having a ring formed by the linkage of nitrogen atoms, such as methylsulfamoyl, dimehtylsulfamoyl, ethylsulfamoyl, diethylsulfamoyl, dibutylsulfamoyl, piperidinosulfamoyl, morpholinosulfamoyl, phenylsulfamoyl, mehtylphenylsulfamoyl, ethylphenylsulfamoyl, benzylphenylsulfamoyl), cyano group, sulfonyl groups (for example, methanesulfonyl, ethanesulfonyl, phenylsulfonyl, 4-chlorophenylsulfonyl, p-toluenesulfonyl), alkoxycarbonyl groups (for example, methoxycarbonyl, ethoxycarbonyl, butoxycarbonyl), aryloxycarbonyl groups (for example, phenoxycarbonyl), acyl groups (for example, acetyl, propionyl, butyroyl, benzoyl, alkylbenzoyl), ureido groups (for example, methylaminocarbonamido, diethylaminocarbonamido), urethane groups (for example, methoxycarbonamido, butoxycarbonamido) and acyloxy groups (for example, acetyloxy, propionyloxy, butyroyloxy).

$A^4$ may further have a substituent which is exemplified above as in $A^4$. It is preferable that the group represented by $A^4$ (optionally substituted) has from 0 to about 36 carbon atoms.

Preferable examples of $A^4$ include alkyl groups, aryl groups, heterocyclic groups, alkoxy groups, aryloxy groups, alkylthio groups, arylthio groups, amino groups, carbonamido groups, ureido groups, urethane groups and halogen atoms. Among all, alkyl groups are particularly preferable therefor. n is an integer of from 0 to 4. When n is 2 or more, $A^4$'s may be either the same or different from each other. When n is 2 or more, $A^4$'s may be bonded together to form a ring. It is preferable that n is 0 or 1.

Examples of $A^5$ and $A^6$ include a hydrogen atom and the groups cited above as the examples of $A^4$. Preferable examples of $A^5$ and $A^6$ include a hydrogen atom, alkyl groups, aryl groups, heterocyclic groups, acyl groups, sulfonyl groups, carbamoyl groups, alkyloxycarbonyl groups, aryloxycarbonyl groups, amino groups and alkyloxy groups. Among all, alkyl groups are particularly preferable. These groups may have further substituents. $A^4$, $A^5$ and $A^6$ may be bonded together to form a ring.

Examples of $A^7$ include a hydrogen atom and the groups cited above as the examples of $A^4$. It is preferable that $A^7$ is a group which adequately leaves as an O═C═N—$A^7$ molecule together with the coupler leaving group after the formation of a color developing agent precursor from a color developing agent and a coupler so as to form a dye. Examples of such a group include a hydrogen atom, alkyl groups, aryl groups, heterocyclic groups, sulfonyl groups, carbamoyl groups, alkyloxycarbonyl groups, aryloxycarbonyl groups, amino groups, alkyloxy groups and aryloxy groups. Among all, a hydrogen atom and alkyl, aryl and heterocyclic groups are preferable as $A^7$.

$A^8$ represents —O—, —S—, —$N(A^{11})$— or —$C(A^{12})(A^{13})$. $A^9$ represents ═O, ═S, ═N—$A^{14}$ or ═$C(A^{15})$—$C(A^{16})$═N—$A^{17}$. Examples of $A^{10}$ to $A^{17}$ include the groups cited above as the examples of $A^4$. It is favorable that the group formed by $A^8$ to $A^{10}$ and the carbon atom is a group which appropriately leaves from the color developing agent precursor represented by general formula (VI) under heating or the action of another compound to thereby form a color developing agent. Examples thereof include groups represented by the following general formulae (XIII) to (XVI):

(XIII)

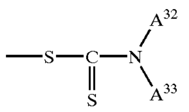

(XIV)

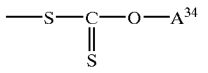

(XV)

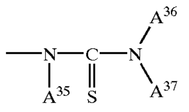

(XVI)

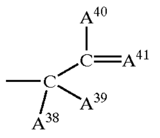

In general formulae (XIII) to (XVI) $A^{32}$ to $A^{40}$ are substituents while $A^{41}$ is as defined in the illustration of $A^9$. Preferable examples of $A^{32}$ to $A^{40}$ include alkyl groups, aryl groups, heterocyclic groups, sulfonyl groups, carbamoyl groups, alkyloxycarbonyl groups, aryloxycarbonyl groups, amino groups, alkyloxy groups and aryloxy groups. Among all, alkyl groups are particularly preferable therefor. Among the groups represented by general formulae (XIII) to (XVI), those of general formula (XIII) are particularly preferable.

Next, particular examples of the compounds represented by general formula (I) will be listed. However it is to be understood that the invention is not construed as being limited thereto.
I-1
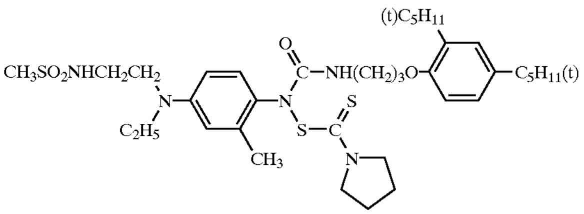
I-2
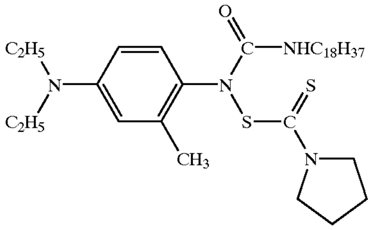
I-3
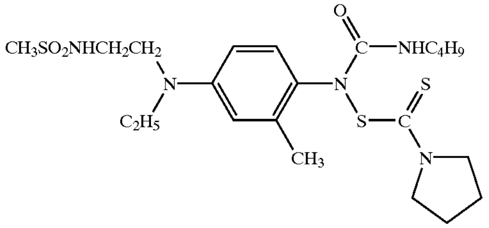
I-4
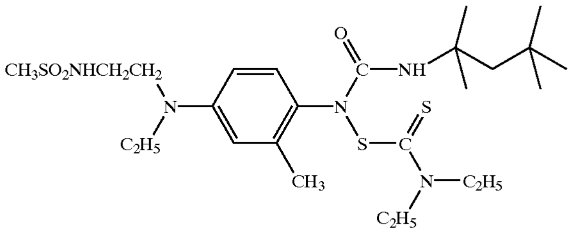
I-5
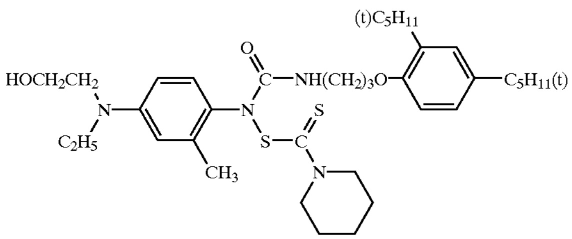
I-6
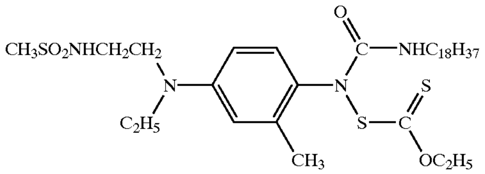
-continued
I-7
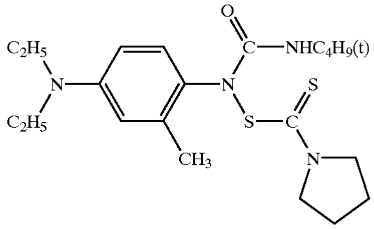
I-8
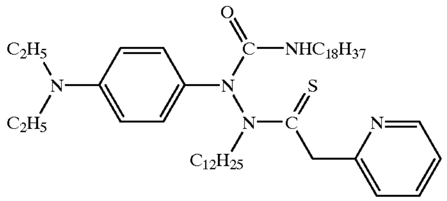
I-9
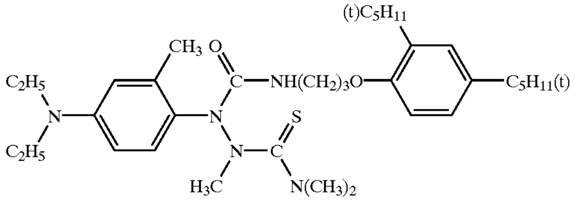
I-10
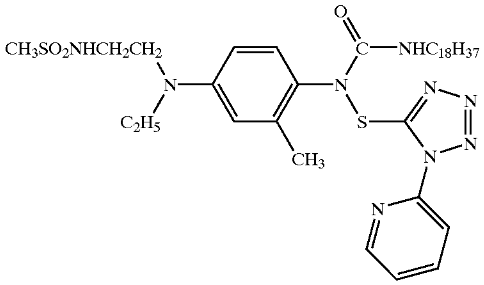
I-11
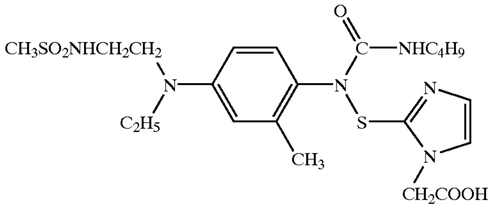
I-12
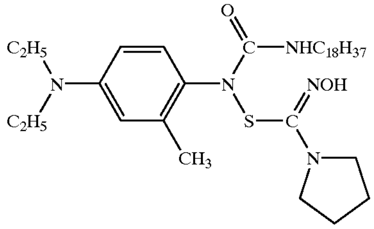

-continued
I-13
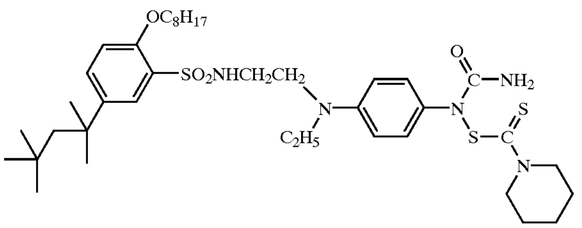
I-14
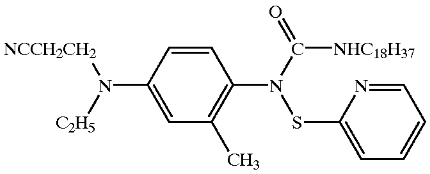
I-15
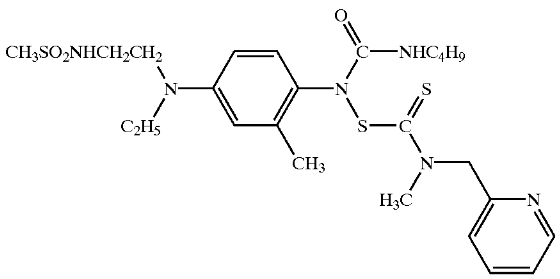
I-16
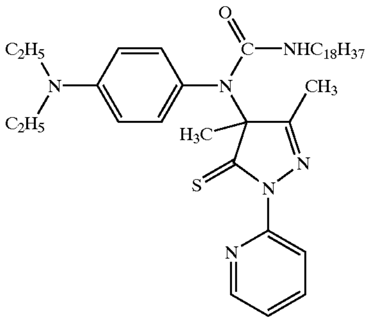
I-17
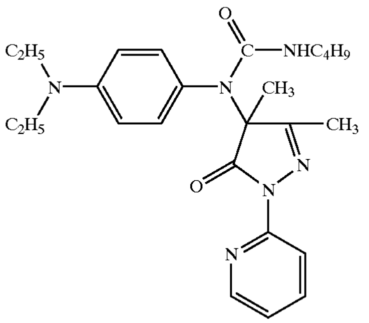
-continued
I-18
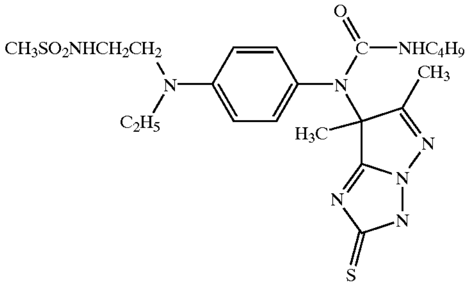
I-19
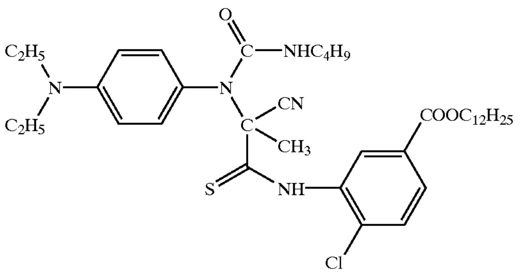
I-20
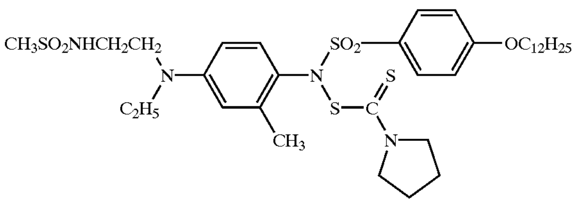
I-21
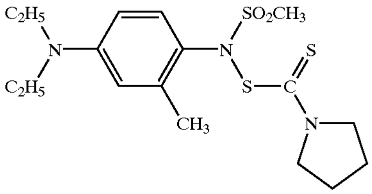
I-22
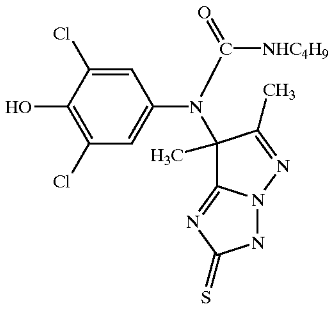
I-23
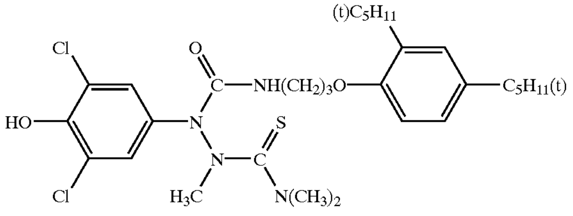

-continued

I-24

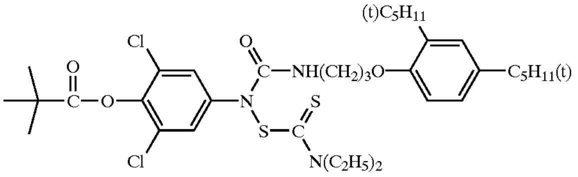

I-25

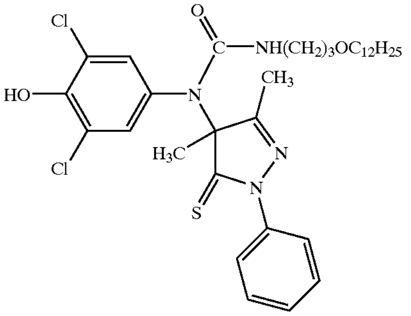

I-26

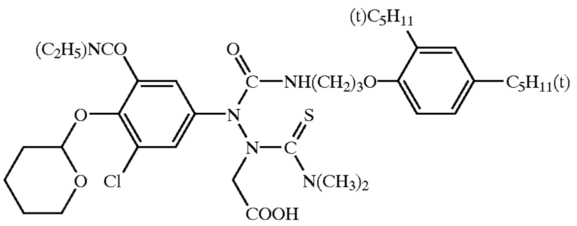

I-27

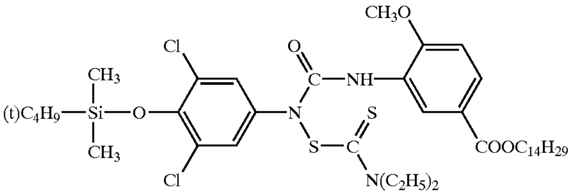

I-28

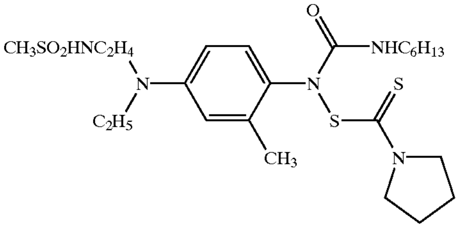

I-29

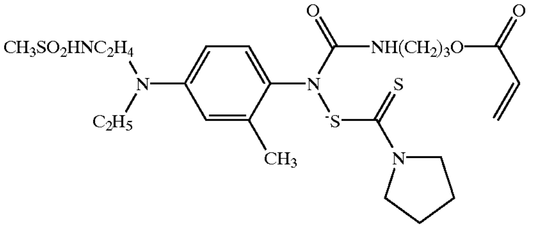

-continued

I-30

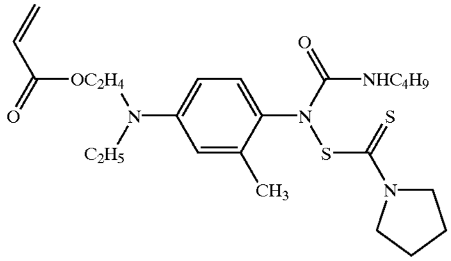

I-31

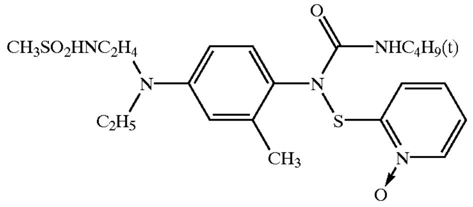

I-32

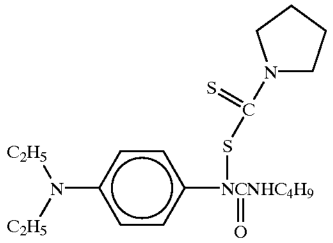

The compound represented by general formula (VI) according to the invention may be synthesized usually by two routes. Namely, one route (1) whereby the compound of general formula (VI) is synthesized starting from a color developing agent of general formula (VI-1) via a compound of general formula (VI-2); and the other route (2) whereby the compound of general formula (VI) is synthesized starting with a color developing agent of general formula (VI-1) via a compound of general formula (VI-3).

Route (1)

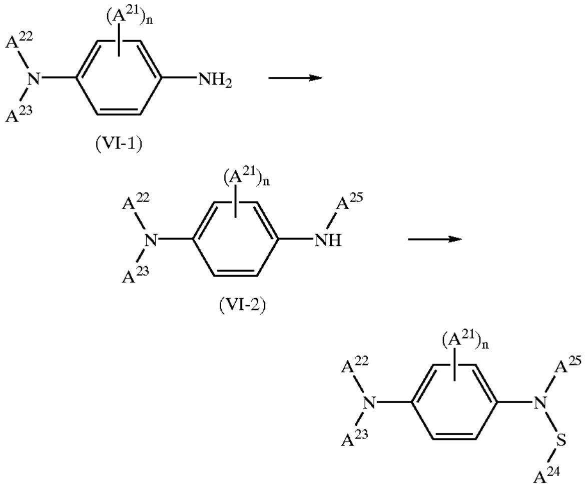

(VI-1) (VI-2) (VI)

Route (2)

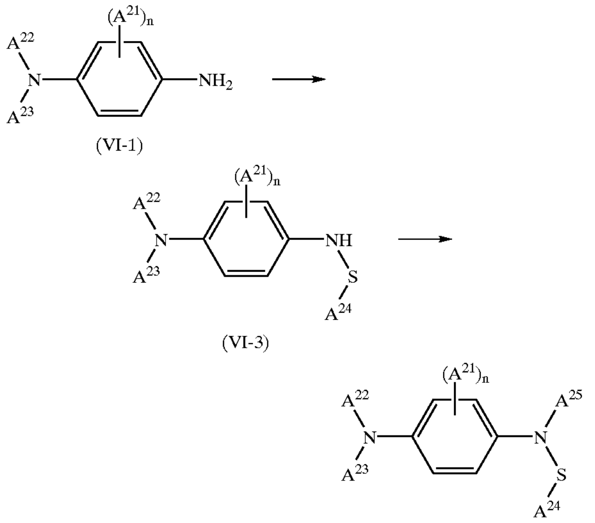

(VI-1)

(VI-3)

(VI)

The compound of general formula (VI-2) can be synthesized from the color developing agent of general formula (VI-1) usually by reacting the color developing agent of general formula (VI-1) or its salt (for example, hydrochloride, sulfate) with X—$A^{25}$ (wherein X represents a leaving group such as a halogen atom, a phenoxy group or an acyloxy group) or an equivalent thereof (for example, isocyanate) The reaction solvent to be used therein may be appropriately selected from among publicly known solvents such as ethyl acetate, chloroform, methylene chloride, acetonitrile, isopropyl alcohol, tetrahydrofuran, toluene and N,N-dimethylacetamide. In this reaction, it is also possible, if needed, to use a base such as triethylamine, pyridine, ammonia, pyrrolidine, DBU, sodium hydride, t-butoxypotassium, potassium carbonate or aqueous solution of sodium hydrogencarbonate. When the compound represented by X—$A^{25}$ can be hardly obtained, it is also possible that a compound of general formula (VI-4) or general formula (VI-5) (wherein X presents a leaving group such as a halogen atom, a phenoxy group or an acyloxy group) is synthesized from the compound of general formula (VI) and then reacted with a compound represented by X—$A^{26}$ (in case of the compound of general formula (V-4)), or a compound represented by X—$A^{27}$ (in case of the compound of general formula (VI-5)) to thereby give the aimed compound of general formula (VI-2).

(VI-4)

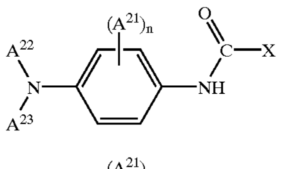

(VI-5)

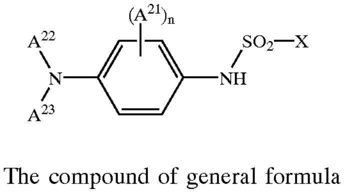

The compound of general formula (VI) can be obtained by reacting the compound of general formula (VI-2) with H—S—$A^{24}$ or itys salt (for example, ammonium salt, sodium salt) in the presence of an oxidizing agent. The reaction solvent to be used therein may be exemplified by those cited above. The oxidizing agent can be appropriately selected from publicly known oxidizing agents such as manganese dioxide, silver acetate, ammonium persulfate, potassium permanganate, iodine and N-chlorosuccinimide. In this reaction, it is also possible to use a base, if needed, examples of which are the same as cited above.

In the route (2) wherein the compound of general formula (VI) is synthesized starting with the color developing agent of general formula (VI-1) via the compound of general formula (VI-3), the color developing agent of general formula (VI-1) or its salt (for example, sulfate, hydrochloride) is reacted with H—S—$A^{24}$ or its salt (for example, ammonium salt, sodium salt) in the presence of an oxidizing agent to give the compound of general formula (VI-3). The reaction solvent, the oxidizing agent and the coexisting base to be used therein are each exemplified by those described above.

The compound of general formula (VI) can be synthesized by reacting the compound of general formula (VI-3) with X—$A^{25}$(wherein X represents a leaving group such as a halogen atom, a phenoxy group or an acyloxy group) or an equivalent thereof (for example, isocyanate). The reaction solvent and the coexisting base to be used there in are each exemplified by those described above.

Once synthesized by such a method, the compound of general formula (VI) may be further modified to thereby give a compound of general formula (VI) which is more appropriate for the desired use. $A^{21}$ to $A^{27}$ employed in illustrating the production methods are the same in the meaning as $A^{21}$ to $A^{27}$ defined in illustrating general formula (VI).

Next, examples of methods for producing the compounds represented by general formula (I) will be described in detail.

SYNTHESIS EXAMPLE 1

Synthesis of Compound (I-1)

100 g (271 mmol) of the color developing agent (1-A) was dissolved in a liquid mixture of 500 ml of ethyl acetate with 1,000 ml of water. To the obtained solution were added 136 g (1.62 mol) of sodium hydrogencarbonate and 38.14 g (244 mmol) of phenyl chloroformate. After-stirring for 1 hour, the organic layer was collected, dried over anhydrous magnesium sulfate and concentrated under reduced pressure. Next, 500 ml of acetonitrile and 74.65 g (265 mmol) of the amine (1-B) were added and the resultant mixture was heated under reflux for 2 hours. After concentrating the liquid reaction mixture under reduced pressure, 1 l of methanol and 100 ml of water were added to the residue and the crystals thus precipitated were collected by filtration to thereby give 110.4 g (187 mmol) of a color developing agent (1-C).

100 g (170 mmol) of the color developing agent (1-C) was dissolved in 600 ml of ethyl acetate and 55.80 g (340 mmol) of ammonium pyrrolidine-N-dithiocarbamate and 700 g of manganese dioxide were added thereto. After stirring for 2 hours, the liquid reaction mixture was filtered and purified by silica gel chromatography to give 65 g (88.5 mmol) of the compound (I-1).

NMR spectrum of compound (I-1):

NMR ($CDCl_3$): δ=8.00 (d, 1H), 7.16 (s, 1H), 7.09 (d, 1H), 6.79 (d, 1H), 6.55 (s, 1H), 6.44 (d, 1H), 5.29 (br, t, 1H), 4.52 (br, t, 1H), 4.01 (br, 2H), 3.89 (br, 2H), 3.70–3.15 (m, 10H), 2.94 (s, 3H), 2.21 (s, 3H), 2.15–1.45 (m, 10H), 1.30 (s, 6H), 1.24 (s, 6H), 1.11 (t, 3H), 0.67 (t, 3H), 0.54 (t, 3H).

(1-A)

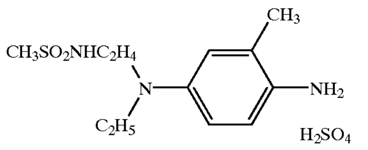

(1-B)

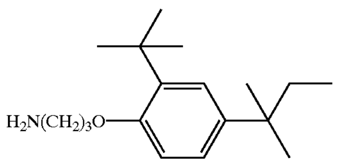

(1-C)

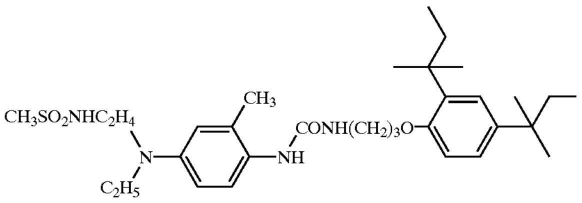

SYNTHESIS EXAMPLE 2

Synthesis of Compound (I-2)

20 g (93 mmol) of the following color developing agent (2-A) was dissolved in a liquid mixture of 100 ml of ethyl acetate with 200 ml of a saturated aqueous solution of sodium hydrogencarbonate. To the obtained solution was added 27.52 g (93 mmol) of octadecyl isocyanate. After stirring for 1 hour, the crystals thus precipitated were collected by filtration, washed with water and ethyl acetate and dried. Thus, 40.3 g (85.1 mmol) of the color developing agent (2-B) was obtained. 10.0 g (21.1 mmol) of the color developing agent (2-B) and 6.93 g (42.2 mmol) of ammonium pyrrolidine-N-dithiocarbamate were dissolved in 60 ml of dichloromethane. After adding 60 g (690 mmol) of manganese dioxide, the resultant mixture was stirred for 1 hour. Then the liquid reaction mixture was filtered through celite and the filtrate was purified by silica gel chromatography to thereby give 4.43 g (7.16 mmol) of the compound (I-2).

NMR spectrum of compound (I-2):

NMR ($CDCl_3$): δ=8.00 (d, 1H), 6.46 (br, 2H), 5.00 (br, t, 1H), 4.10–3.40 (br, 4H), 3.37 (q, 4H), 3.25 (q, 2H), 2.24 (s, 3H), 2.15–1.80 (m, 4H), 1.55–1.00 (m, 38H), 9.90 (t, 3H).

(2-A)

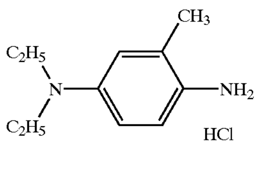

(2-B)

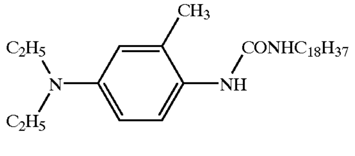

SYNTHESIS EXAMPLE 3

Synthesis of Compound (I-6)

10 g (17.6 mmol) of the color developing agent (6-A) synthesized as in Synthesis Example 2 and 4.24 g (26.5 mmol) of potassium ethylxanthate were suspended in methylene chloride. After adding 40 g of manganese dioxide, the resultant mixture was stirred for 1 hour. Then the liquid reaction mixture was filtered and purified by silica gel chromatography to give 10 g (14.6 mmol) of the compound (I-6).

NMR spectrum of compound (I-6):

NMR ($CDCl_3$): δ=7.31 (d, 1H), 6.70–6.40 (br, 2H), 5.03 (br, t, 1H), 4.74 (q, 2H), 4.53 (br, t, 1H), 3.70–3.10 (m, 8H), 2.98 (s, 3H), 2.18 (s, 3H), 1.70–1.18 (m, 32H), 1.18 (t, 3H), 0.99 (t, 3H).

(6-A)

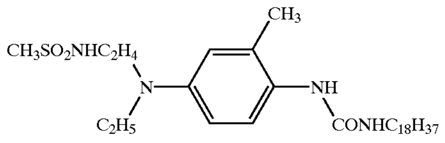

SYNTHESIS EXAMPLE 4

Synthesis of Compound (I-32)

18 g (109.8 mmol) of the color developing agent (32-A) was dissolved in 200 ml of ethyl acetate and 27 g (164.3 mmol) of ammonium pyrrolidine—N-dithiocarbamate was added thereto. Next, 90 g (1.035 mol) of manganese dioxide was added under ice-cooling and the resultant mixture was stirred for 30 minutes. Then the liquid reaction mixture was filtered and purified by silica gel chromatography to thereby give 3 g (9.69 mmol) of the compound (32-B). This product was dissolved in 30 ml of butyl isocyanate and stirred at room temperature for 2 weeks. The liquid reaction mixture was purified by silica gel chromatography to give 0.91 g (2.23 mmol) of the compound (I-32).

NMR spectrum of compound (I-32):

NMR ($CDCl_3$): δ=7.49 (d, 2H), 6.58 (d, 2H), 5.10 (br, t, 1H), 4.10–3.00 (m, 10H), 2.20–1.80 (m, 4H), 1.48 (m, 2H), 1.31 (m, 2H), 1.18 (t, 6H), 0.91 (t, 3H).

(32-A)

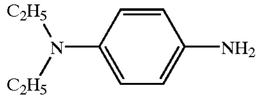

(32-B)

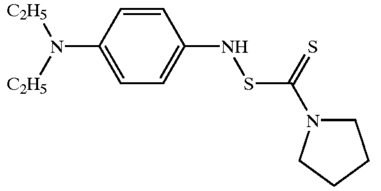

SYNTHESIS EXAMPLE 5

Synthesis of Listed Compound (I-17)

20.79 g (79.27 mmol) of the compound (17-A) and 15 g (79.27 mmol) of the compound (17-B) were dissolved in a liquid mixture of 100 ml of ethyl acetate with 300 ml of a saturated aqueous solution of sodium hydrogencarbonate. Next, 21.71 g (95.12 mmol) of ammonium persulfate was added thereto. Then the organic layer was collected, dried over anhydrous sodium sulfate and concentrated under reduced pressure. After purifying by alumina column chromatography, 16 g (45.5 mmol) of the compound (17-C) was obtained.

Compound (17-A)

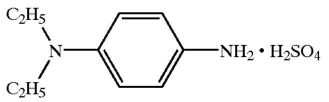

Compound (17-B)

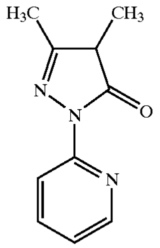

Compound (17-C)

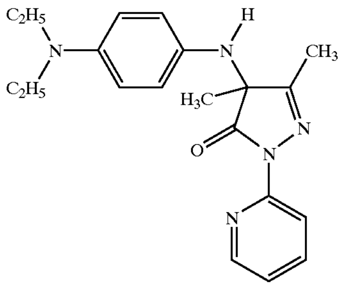

15 g (42.7 mmol) of the compound (17-C) was dissolved in 30 ml of butyl isocyanate and then stirred at 50° C. for 72 hours. The liquid reaction mixture was purified by silica gel chromatography to give 1.8 g (3.99 mmol) of the compound (I-17).

Coupler

In the invention, a coupler reacts with the activated color developing agent as described above to form a dye. As the coupler, use can be made of either 4-equivalent coupler or 2-equivalent coupler employed in the field of silver halide photographic photosensitive materials. It is still preferable to use the 2-equivalent couplers as the coupler. In case where use is made of a compound of general formula (II) wherein $A^2$ is represented by general formula (X) and W is $—SO_2—$, it is preferable to combine the compound with the 4-equivalent coupler.

As the coupler, it is favorable to use couplers described or cited in JP—A-08-286340 (columns 0098–0145) and preferable examples thereof are the same as those cited as preferable example in this document (the term "JP—A" as used herein means an "unexamined published Japanese-patent application"). It is also possible to use the compounds C-1 to C-80 listed in this document (column 0130-0145) as preferable examples of the coupler.

Activator

In the dye-forming method, the color developing compositions and the photosensitive materials according to the invention, use can be made of, together with the color developing agent precursor and the coupler as described above, an activator which acts on the color developing agent precursor to form a color developing agent. As the activator, it is preferable to use an activator with the utilization of a nucleophilic addition reaction or a nucleophilic substitution reaction of $A^3$ in the color developing agent precursor with an atom in the activator, or an activator with the utilization of the affinity of $A^3$ for the metal atom.

Examples of the activator with the use of the nucleophilic reaction are as follows.

(E-1)

$Br—CH_2CO_2C_4H_8OCOCH$ (E-2)

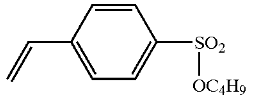

(E-3)

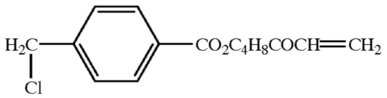

(E-4)

$(C_7H_{15}CO)_2O$ (E-5)

$(C_7H_{15}CHO$ (E-6)

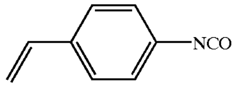

(E-7)

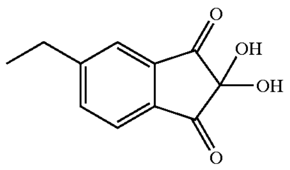

(E-8)

$CH_3COCHO$ (E-9)

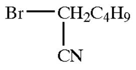

(E-10)

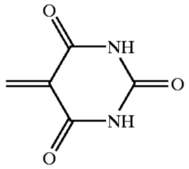

(E-11)

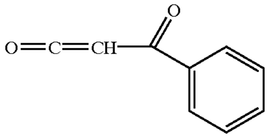

(E-12)

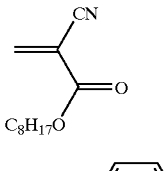

(E-13)

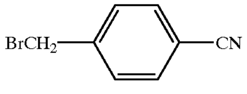

(E-14)

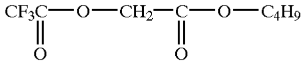

(E-15)

$I—C_8H_{17}$

In the invention, the electrophile may be employed at an arbitrary molar ratio to the color developing agent precursor. It is preferable to use the electrophile in an amount (1/10) to 100 times by mol, still preferably (1/2) to 20 times by mol and most desirably 1 to 10 times by mol, as much as the color developing agent precursor.

In case of using an activator containing a metal atom, a compound represented by general formula (Q) is employed. As such an activator, compounds represented by the following general formula (IV) are still preferable in view of improving the oil-solubility of the activator and preventing printout caused by light.

$$(M^{n+})_p(A)_q(B)_r \qquad \text{(IV)}$$

In the above general formula (IV), M represents a metal atom having an electric charge n, and n is an integer of from 0 to 7, preferably from 0 to 3.

Preferable examples of the metal atom M include titanium, vanadium, chromium, manganese, iron, cobalt, nickel, copper, zinc, zirconium, molybdenum, ruthenium, rhodium, palladium, silver, cadmium, mercury, tin, tungsten, rhenium, osmium, iridium, platinum, gold, mercury, thallium, lead and uranium. Among all, preferable examples are titanium, vanadium, manganese, iron, copper, zinc, zirconium, molybdenum, palladium, silver, tin, tungsten, iridium, platinum, gold and lead; still preferable examples are titanium, vanadium, manganese, iron, zinc, zirconium, silver, copper and tin; and copper, zinc and silver are the most desirable ones.

In general formula (IV), A represents an atomic group having a negative electrical charge of 1 to 7 which neutralizes the electrical charge of the metal atom represented by M. It is preferable that A is an atomic group containing an organic anion such as a carboxylic aid anion, a sulfonic acid anion, a sulfuric acid monoester anion, a phosphoric acid diester anion, a β-ketoester anion, a β-diketone anion, an oxime anion, a hydroxamic acid anion or a tetraphenylboric acid anion; or an inorganic anion such as a halide anion, a sulfuric acid anion, a nitric acid anion, a phosphoric acid anion, a phosphorus hexafluoride anion or aboron tetrafluoride anion. Among all, preferable examples of the atomic group represented by A include those containing a carboxylic aid anion, a sulfonic acid anion, a sulfuric acid monoester anion, a β-ketoester anion, a β-diketone anion, a halide anion, a phosphorus hexafluoride anion or a boron tetrafluoride anion, and an atomic group containing a boron tetrafluoride anion is the most desirable one.

In general formula (IV), p is an integer of from 1 to 24 while q is an integer of from 0 to 24. It is particularly preferable that the ratio p/q ranges from 1/6 to 6, still preferably from 1/3 to 3. When q is 2 or more, two or more A's maybe either the same or different, or bonded to each other to form a structure.

In general formula (IV), B represents an atomic group represented by the following general formula (V), and r is an integer of from 1 to 24. When r is 2 or more, two or more B's may be either the same or different, or bonded to each other to form a structure. It is preferable that the ratio r/p ranges from 1/6 to 6, still preferably from 1/3 to 3.

(V)

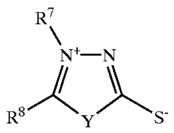

In general formula (V), Y represents O, S or N—$R^9$. It is particularly preferable that Y is N—$R^9$.

In general formula (V), $R^7$ and $R^9$ represent each a substituent, and $R^8$ represents a hydrogen atom or a substituent. Preferable examples of the substituents represented by $R^7$, $R^8$ and $R^9$ include those cited as preferable examples of the substituents represented by $R^3$ to $R^6$. It is particularly preferable that $R^7$ and $R^9$ are each an alkyl group, an aryl group or a heterocyclic group, while $R^8$ is a hydrogen atom, an alkyl group, an aryl group or a heterocyclic group. Alternatively, $R^7$ and $R^8$, and $R^8$ and $R^9$ may be respectively bonded together to form rings.

To the compound represented by general formula (IV), another atomic group substantially not neutralizing electrical charges of other groups (for example, a neutral molecules such as $H_2O$ or $NH_3$, a diplor ion molecule) may be further attached via, for example, a coordinate bond. Also, the compound represented by general formula (IV) may be a double salt having the composition of general formula (IV).

Next, examples of the activator containing a metal atom will be listed. However, it is to be understood that the metal salts usable in the invention are not restricted to these compounds listed below. Among the compounds represented by general formula (IV), examples of the partial structure represented by $(M^{n+})_p(A)_q$ will be shown in II'-1 to II'-30, while examples of the partial structure represented by B will be shown in III-1 to III-15. Examples of the compounds represented by general formula (V) include all of the compounds having these two partial structures combined at an arbitrary ratio and particular examples thereof will be shown in II-1 to II-4.

Examples of partial structure represented by $(M^{n+})_p(A)_q$:

II'-2

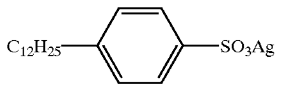

II'-7

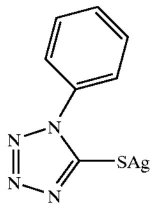

II'-10

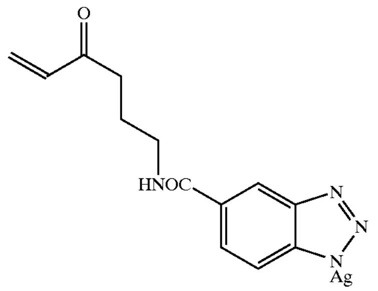

II'-16
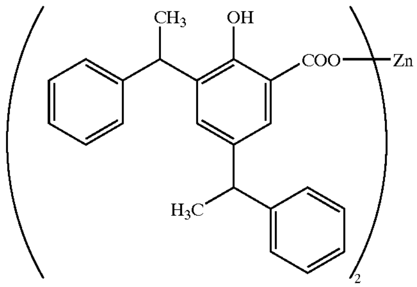
II'-17
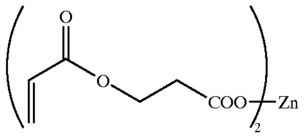
II'-22
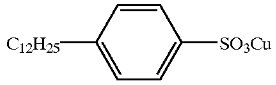
Examples of partial structure represented by general formula (V):
III-1
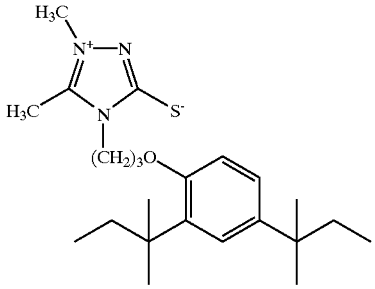
III-2
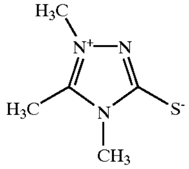
III-3
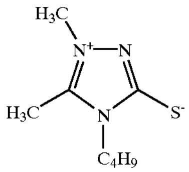
III-4
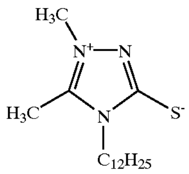
-continued
III-5
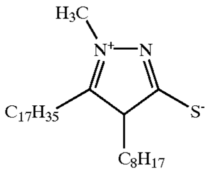
III-6
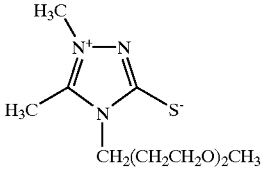
III-7
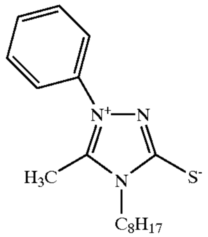
III-8
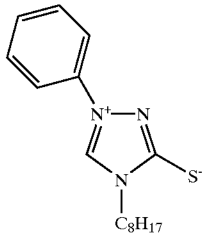
III-9
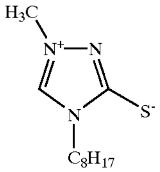
III-10
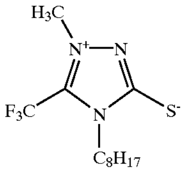
III-11
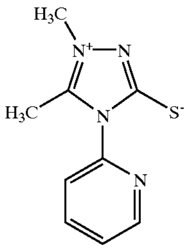

-continued

III-12

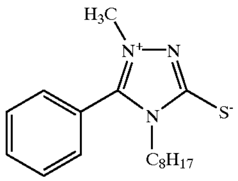

III-13

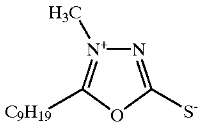

III-14

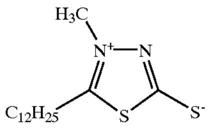

III-15

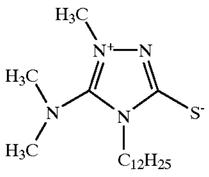

Examples of compound represented by general formula (IV):

II-1

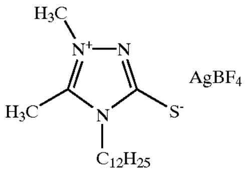

II-2

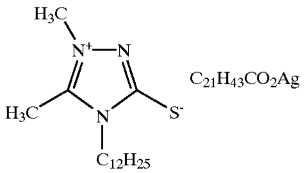

II-3

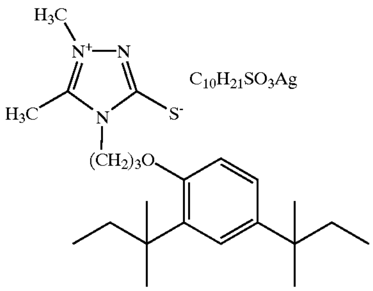

-continued

II-4

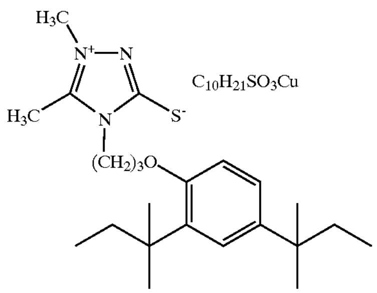

The compound represented by general formula (IV) can be synthesized by mixing the metal salt $(M^{n+})_p(A)_q$ with B represented by general formula (V) at an appropriate ratio in a solvent. The solvent to be used in mixing may be selected from among publicly known solvents by taking, for example, the solubilities of the metal salt and B therein into consideration. For example, use may be made therefor of water, ethyl acetate or methylene chloride. Mixing may be carried out under heating, if desired. The metal salt $(M^{n+})_p(A)_q$ serving as the starting material may be in the isolated state. Alternatively, the metal salt synthesized in the liquid reaction mixture may be mixed with B as such without isolating. It is also possible to synthesize the compound represented by general formula (IV) by an anion exchange method.

The compounds represented by general formula (V) can be synthesized by methods described in, for example, Research Disclosure, vol. 12, 17643 (1979); Research Disclosure, vol. 6, 17029 (1978); J. Org. Chem., vol. 32, 2245 (1976); J. Chem. Soc., 3799 (1959); J. Am. Chem. Soc., vol. 80, 1895 (1958); J. Chem. Soc. Perkin. Trans, I 633 (1974); J. Chem. Soc. Perkin. Trans. I 627 (1974); J. Heterocyclic Chem., vol.2, 105 (1965); J. Heterocyclic Chem., vol.5, 5277 (1968); Chem. Commun., 1222 (1971); Tetrahedron. Lett., 5881 (1968); Tetrahedron. Lett., 1578 (1971); Tetrahedron. Lett., 2933 (1972); Tetrahedron. Lett., 1809 (1967); U.S. Pat. No. 4,478,424; ibid. U.S. Pat. No. 4,631,253; ibid. U.S. Pat. No. 4,675,276; and ibid. U.S. Pat. No. 4,939,075.

Next, detailed examples of the methods for synthesizing the compounds represented by general formula (IV) will be given.

SYNTHESIS EXAMPLE 5

Synthesis of Listed Compound (II-1)

10.64 ml (200 mmol) of methylhydrazine was added under ice-cooling to 20 ml of methanol. Next, 18.87 ml (200 mmol) of acetic anhydride was dropped thereinto. After heating the liquid reaction mixture to 40° C., 45.5 g (200 mmol) of dodecyl isothiocyanate and 50 ml of acetonitrile were added and the resultant mixture was stirred at 50° C. for 2 hours. After cooling to room temperature, the crystals were collected by filtration to give 44.4 g (141 mmol) of a compound $(CH_3CON(CH_3)NH(C{=}S)NHC_{12}H_{35})$. 34.3 g (109 mmol) of this compound was suspended in 100 ml of methanol and 400 $\mu$g of a 28% methanol solution of sodium methoxide was added thereto. After stirring at 60° C. for 10 minutes, the liquid reaction mixture was cooled by allowing to stand. The crystals were collected by filtration and washed with methanol to thereby give 30.4 g (102 mmol) of the compound (III-4).

NMR ($CDCl_3$): δ=4.08, 3.78 (s, 3H), 2.58 (s, 3H), 1.90–1.60 (m, 2H), 1.50–1.10 (br, 18H), 0.88 (t, 3H).

3.22 g (10.8 mmol) of the compound (III-4) thus obtained was suspended in 10 ml of ethyl acetate and 2.63 g (13.5 mmol) of silver tetrafluoroborate was added. As a result, an exothermic reaction arose and a homogeneous solution in a slightly yellow color was formed. After washing with 20 ml portions of water twice, the solution was dehydrated over anhydrous magnesium sulfate. Next, 50 ml of hexane was added and the crystals thus formed was collected by filtration and washed with hexane. Thus, 5.0 g (10.2 mmol) of the compound (II-1) was obtained as slightly yellow-colored crystals.

NMR ($CDCl_3$): δ=4.06 (t, 2H), 3.70 (s, 3H), 2.60 (s, 3H), 1.90–1.60 (m, 2H), 1.50–1.10 (br, 18H), 0.88 (t, 3H). Elemental analysis: H 6.27% (calcd. 6.36%), C 39.90% (calcd. 39.04%), N 8.54% (calcd. 8.54%).

SYNTHESIS EXAMPLE 6

Synthesis of Listed Compound (II-2)

665 mg (2.23 mmol) of the compound (III-4) obtained as in Synthesis Example 5 and 1 g of behenic acid were suspended in 30 ml of ethyl acetate and the resultant mixture was heated under reflux for 10 minutes. After cooling to 40° C. by allowing to stand, the insoluble matters were filtered off and the filtrate was ice-cooled. The crystals thus precipitated were collected by filtration and washed with cold ethyl acetate to thereby give 1.4 g (1.88 mmol) of the compound (II-2).

NMR ($CDCl_3$): δ=4.11 (t, 2H), 3.88 (s, 3H), 2.66 (s, 3H), 2.24 (t, 2H), 1.90–1.10 (br, 58H), 0. 89 (t, 6H).

SYNTHESIS EXAMPLE 7

Synthesis of Listed Compound (II-3):

1.8 g (5.47 mmol) of silver decanesulfonate and the compound (III-1) obtained as in Synthesis Example 5 were suspended in 20 ml of ethyl acetate and the resultant mixture was heated under reflux for 5 minutes. After cooling to room temperature by allowing to stand, the insoluble matters were filtered off and the filtrate was concentrated under reduced pressure to thereby give 3.7 g (5.05 mmol) of the compound (II-3).

NMR ($CDCl_3$): δ=7.16 (s, 1H), 7.09 (d, 1H), 6.80 (d, 1H), 4.43 (t, 2H), 4.05 (t, 2H), 3.92 (s, 3H), 2.80–2.50 (br, 5H), 2.50–2.25 (br, 2H), 2.00–1.05 (br, 32H), 0.87 (t, 3H), 0.75–0.50 (m, 6H).

SYNTHESIS EXAMPLE 7

Synthesis of Listed Compound (II-4)

182 mg (0.743 mmol) of sodium decanesulfonate, 73.6 mg (0.743 mmol) of copper chloride and the compound (III-1) obtained as in Synthesis Example 5 were suspended in a liquid mixture of 20 ml of ethyl acetate with 30 ml of water and the resultant mixture was heated under reflux for 5 minutes. After cooling to room temperature by allowing to stand, the formed crystals were collected by filtration to thereby give 550 mg (0.468 mmol) of the compound (II-4).

NMR ($CDCl_3$): δ=7.17 (s, 1H), 7.08 (d, 1H), 6.79 (d, 1H), 4.45 (t, 2H), 4.06 (t, 2H), 3.96 (s, 3H), 2.90–2.55 (br, 5H), 2.55–2.30 (br, 2H), 1.80–1.10 (br, 32H), 0.87 (t, 3H), 0.80–0.50 (m, 6H).

The dye-forming method according to the invention is usable as a photosensitive material in forming an image, as will be described hereinafter. It is also usable as an image forming method by using a separation method by employing, for example, heat-responsible capsules and a heating method by employing a thermal head.

When the photosensitive material is used in the dye-forming method of the invention, it is preferable that the photosensitive material contains a polymerizable compound and a polymerization initiator, in addition to the color developing agent precursor, the dye-forming coupler and the activator. However, the polymerizable compound may be the same molecule as the color developing agent precursor, the dye-forming coupler or the activator.

Polymerizable Compound

The polymerizable compound to be used in the invention is a compound which undergoes polymerization due to the action of a polymerization initiator contained in the photosensitive material when exposed to light and thus hardens. By the polymerization of this polymerizable compound, the mobility of at least one of the color developing agent precursor, the activator and the coupler is lowered.

As the polymerizable compound, use can be made of publicly known compounds having polymerizable groups. Examples thereof include acrylic acid and its salts, acrylic acid esters and acrylamides; methacrylic acid and its salts, methacrylic acid esters and methacrylamides; maleic anhydride and maleic acid esters; itaconic acid and itaconic acid esters; styrenes; vinyl ethers; vinyl esters; N-vinylheterocyclic compounds; aryl ethers; and allyl esters. Among these polymerizable vinyl monomers, those having two or more vinyl groups per molecule are particularly preferable. Namely, particularly preferable examples thereof include acrylates and methacrylates of polyhydric alcohols such as trimethylolpropane and pentaerythritol; acrylates and methacrylates of polyhydric phenols and bisphenols such as resorcinol, pyrogallol and phloroglucinol; and epoxy resins having terminal acrylate or methacrylate groups and polyesters having terminal acrylate or methacrylate groups. As particular examples thereof, citation may be made of ethylene glycol diacrylate, ethylene glycol dimethacrylate, trimethylolpropane triacrylate, pentaerythritol tetraacrylate, dipentaerythritol hydroxypentaacrylate, hexanediol-1,6-dimethacrylate and diethylene glycol dimethacrylate.

It is also possible that polymerizable group(s) are introduced into one of the color developing agent precursor, the coupler and the activator as described above so that it serves as the polymerizable compound too.

Photopolymerization Initiator

In the invention, the polymerization initiator has a function of initiating the polymerization reaction of the polymerizable compound contained in the photosensitive material due to light irradiation. The polymerization initiator may be appropriately selected from among various materials by taking the combination with the polymerizable compound into consideration. For example, use may be made therefor of compounds capable of generating a radical by Norrish I type reaction whereby the bond between a carbonyl group and the adjacent carbon atom is cleaved (for example, benzoin alkyl ether); compounds undergoing direct photodecomposition (for example, oxime esters, peroxides, organosulfur compounds, halides, phosphine oxide compounds); aromatic ketones forming a ketyl radical through a hydrogen abstraction reaction (for example, benzophenone); combinations of a donor with an acceptor whereby an exciplex is formed and electron transfer and proton transfer arise, thereby forming a radical (for example, a combination of a ketone with an amine); and photo-redox systems wherein a radical is generated in a complex system having a dye and a weak reducing agent. In addition, compounds described in "Chemical Review" (Monroe et al.), vol. 93, 435–446 (1993) are also usable therefor.

Among these polymerization initiators, those having sensitivity in the visible region are favorable, since various visible ray sources (for example, visible laser beams, LEDs, white fluorescent lamps) can be used in these cases. Japanese Patent No. 2726258 discloses polymerization initiators composed of cationic dye/anionic boron compound complexes as polymerization initiators having sensitivity in the visible region. These polymerization initiators are usable as the polymerization initiator in the invention. Among all, cationic dye/anionic boron compound complexes represented by the following general formula (A) are preferable.

(A)

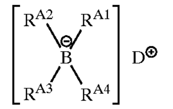

In general formula (A), $R^{A1}$, $R^{A2}$, $R^{A3}$ and $R^{A4}$ represent each a halogen atom, a substituted or unsubstituted alkyl group, a substituted or unsubstituted alkenyl group, a substituted or unsubstituted alkynyl group, an alicyclic group, a substituted or unsubstituted aryl group, a substituted or unsubstituted alkalyl group, a substituted or unsubstituted aryloxyl group, a substituted or unsubstituted aralkyl group, a substituted or unsubstituted heterocyclic group or a substituted or unsubstituted sily group, provided that $R^{A1}$, $R^{A2}$, $R^{A3}$ and $R^{A4}$ are either the same or different or two or more of them may be bonded together to form a cyclic structure.

Preferable examples of the organic borate salt compound moiety in general formula (A) include borate anions such as tetrabutylborate, triisobutylmethylborate, di-n-butyl-di-t-butylborate, tetra-n-butylborate, tetraphenylborate, tetra-p-chlorophenylborate, tetra-m-chlorophenylborate, tri-m-chlorophenyl-n-hexylborate, triphenylmethylborate, triphenylethylborate, triphenylpropylborate, triphenyl-n-butylborate, trimesitylbutylborate, tritolylisopropylborate, tirphenylbenzylborate, tetraphenylborate, tetrabenzylborate, tirphenylphenethylborate, di($\alpha$-naphthyl)-dipropylborate, triphenylsilyltriphenylborate, tritoluylsilyltriphenylborate and tri-n-butyl(dimethylphenylsilyl)borate.

In general formula (A), $D^+$ represents a cationic dye. The cationic dye is not particularly restricted, so long as it has an absorption peak within a region of from the visible light range to 1100 nm wavelength. Namely, a cationic dye may be selected from publicly known ones depending on the purpose. Adequate examples thereof include methine dyes, carbonium dyes, indoline dyes, quinoneimine dyes, and styryl dyes. As the methine dyes, methine dye, polymethine dye, cyanine dye and azamethine dye are preferable and cyanine dye, carbocyanine dye, dicarbocyanine dye, tricarbocyanine dye, hemicyanine dye are particularly preferable. As the carbonium dyes, triarylmethane dye, xanthene dye and acridine dye are preferable and Rhodamine dye is particularly preferable. As the quinoneimine dyes, azine dye, oxazine dye, thiazine dye, quinoline dye and thiazole dye are preferable. Either one of these organic cationic dyes or a combination of two or more thereof may be employed. Among all, it is preferable that $D^+$ is an organic cationic dye selected from among methine dye, polymethine dye, triarylmethane dye, indoline dye, azine dye, xanthene dye, oxazine dye, acridine dye and styryl dye. It is still preferable that $D^+$ is an organic cationic dye selected from among cyanine dye, hemicyanine dye, Rhodamine dye and azamethine dye.

There are known a number of organic cationic dyes having absorption peak in the wavelength region of visible light or longer. Reference may be made of, for example, dyes described in "Kinosei Shikiso no Kagaku", 393–416 (1981), published by CMC Shuppan; and "Shikizai", 60(4), 212–224 (1987).

In the photosensitive material according to the invention, the color developing agent precursor and the coupler maybe used at an arbitrary molar ratio. It is preferable that the color developing agent precursor/dye-forming coupler molar ratio ranges from 0.01 to 100, still preferably from 0.1 to 10 and the most desirably from 0.5 to 5.

In the photosensitive material according to the invention, the color developing agent precursor and the activator may be used at an arbitrary molar ratio. It is preferable that the activator/color developing agent precursor molar ratio ranges from 0.1 to 100, still preferably from 0.2 to 20 and the most desirably from 0.5 to 10.

In the photosensitive material according to the invention, the polymerizable compound and the color developing agent precursor may be used at an arbitrary molar ratio. It is preferable that the polymerizable compound/color developing agent precursor molar ratio ranges from 0.1 to 1000, still preferably from 1 to 100 and the most desirably from 2 to 50.

In the photosensitive material according to the invention, the polymerization initiator is used preferably in an amount of from 0.01 to 10% by mass of the polymerizable compound.

Each component to be used in the invention may be either a single material or a mixture of two or more thereof.

The photosensitive material according to the invention is usable as an image-forming material. Image-forming material and image-recording method:

The image-forming material of the invention has at least one substrate and a recording layer consisting of one or more layers formed on the substrate, wherein the recording layer contains the photosensitive material according to the invention.

An example of the image-recording method using the image-forming material of the invention is an image-recording method having the step of irradiating the recording layer with light in an image-forming manner so as to form a latent image; and the color developing step of applying heat and/or pressure to the recording layer carrying the latent image formed thereon to thereby form a dye in the unirradiated region. In the latent image-forming step, a radical is generated from the polymerization initiator due to the light irradiation and thus the polymerizable compound is polymerized in the irradiated region. As a result, the polymerizable compound in the irradiated region is hardened to thereby form the latent image. In the color developing step, heat is supplied to the recording layer carrying the latent image formed thereon. In the unirradiated region, the color developing agent precursor, the activator and the coupler in the recording layer, at least one of which has been in the non-contact state, is brought into contact. As a result, the color developing agent precursor is converted into the color developing agent under the action of the activator and, at the same time, the oxidant and the coupler undergo a coupling reaction to form a dye, thereby developing the color. In the irradiated region, on the other hand, the polymerizable compound is hardened and, in its turn, the mobility of one of the color developing agent precursor, the activator and the coupler is lowered. Accordingly, all of the components cannot be contact with each other and thus no dye is formed. Thus, the irradiated region remains colorless.

In the image-forming material according to the invention, the recording layer may have a multi-layer structure. In such a case, the components constituting the photosensitive material may be contained in different layers. In a preferable embodiment, the three components (i.e., color developing agent precursor, activator and coupler) are not contained in a single layer. Namely, at least one of these three components is contained together with the polymerizable compound and the polymerization initiator in a layer. In a still preferable embodiment, the color developing agent precursor, the polymerizable compound and the polymerization initiator are contained together in a same layer while the activator and the coupler are contained together in another layer. The image-forming material may have two or more substrates. In such a case, the recording layers are formed respectively on these substrates. In the preferred embodiment as described above, for example, the first layer containing the color developing agent precursor, the polymerizable compound and the polymerization initiator can be formed on the first substrate, while the second layer containing the activator and the coupler can be formed on the second layer. In this embodiment, the recording layer consists of the first and second layers.

In case where the color developing agent precursor, the activator and the coupler are contained in the same layer, it is favorable that at least one of these three components is separated from other components. For example, it is preferable that one or two of the color developing agent precursor, the activator and the coupler are encapsulated in microcapsules and thus separated from others. By using heat-responsible or pressure-responsible microcapsules, these components can be brought into contact with each other under the application of heat or pressure in an image-forming manner, thereby forming the desired image.

In case where the recording layers of the image-forming material of the invention are formed separately on two or more substrates, it is unnecessary to subject the image-forming material in an integrated state to the image-forming step. That is to say, it is possible in the image-forming material of the preferable embodiment as described above, for example, that the first layer alone is irradiated with light in the latent image-forming step. Then, the first and second layers are brought into contact with each other in the color developing step and the thus integrated image-forming material is heated.

In the above recording layer, the color developing agent precursor, the activator and the coupler (hereinafter, these three components will be sometimes referred to as the "dye-forming components") can be introduced into the recording layer with the use of various publicly known dispersion methods reported in, for example, JP-A-07-104448 (column 71, line 3 to column 72, line 11). For example, it is preferable to use the oil droplet-in-water dispersion method wherein these dye-forming components are dissolved in a high-boiling organic solvent (optionally together with a low-boiling organic solvent) and then emulsified and dispersed in an aqueous gelatin solution. The oil droplet-in-water dispersion method is described in detail in U.S. Pat. No. 2,322,027 and it is favorable to employ this method. Examples of the high-boiling organic solvent usable in the oil droplet-in-water dispersion method as described above include phthalic acid esters (for example, dibutyl phthalate, dioctyl phthalate, dicyclohexyl phthalate, di-2-ethylhexyl phthalate, decyl phthalate, bis(2,4-di-tert-amylphenyl) isophthalate), phosphoric acid or phosphone esters (for example, diphenyl phosphate, triphenyl phosphate, tricresyl phosphate, 2-ethylhexyldiphenyl phosphate, dioctylbutyl phosphate, tricyclohexyl phosphate, tri-2-ethylhexyl phosphate, tridecyl phosphate, di-2-ethylhexylphenyl phosphate), benzoic acid esters (for example, 2-ethylhexyl benzoate, 2,4-dichlorobenzoate, dodecyl benzoate, 2-ethylhexyl-p-hydrodybenzoate), amides (for example, N,N-diethyldodecanamide, N,N-diethyllaurylamide), alcohols (for example, isostearyl alcohol), fatty acid esters (for example, dibutoxyethyl succinate, di-2-ethylhexyl succinate, 2-hexyldecyl tetradecanoate, tributyl citrate, diethyl azelate, isostearyl lactate, triocyl citrate), aniline derivatives (for example, N,N-dibutyl-2-butoxy-5-tert-octylaniline), chlorinated paraffins (paraffins containing 10 to 80% of chlorine), trimesic acid esters (for example, tributyl trimesate), dodecylbenzene, diisopropylnaphthalene, phenols (for example, 2,4-di-tert-amylphenol, 4-dodecyloxyphenol, 4-dodecyloxycarbonylphenol, 4-(4-dodecyloxyphenylsulfonyl)phenol), carboxylic acids (for example, 2-(2,4-di-tert-amylphenoxybutyric acid, 2-ethoxyoctanedecanoic, acid), and alkylphosphoric acids (for example, di-2(ethylhexyl)phosphoric acid, diphenylphosphoric acid). It is also possible to use an organic solvent having a boiling point of from 30° C. to about 160° C. (inclusive) (for example, ethyl acetate, butyl acetate, ethyl propionate, methyl ethyl ketone, cyclohexanone, 2-ethoxyethyl acetate, dimethylformamide) as an auxiliary solvent.

It is also possible to use high-boiling organic solvents (for example, those described in U.S. Pat. No. 4,555,470, ibid. U.S. Pat No. 4,536,466, ibid. U.S. Pat. No. 4,536,467, ibid. U.S. Pat. No. 4,587,206, ibid. U.S. Pat. No. 4,555,476, ibid. U.S. Pat. No. 4,599,296, JP-B-3-62,256: the term "JP-B" as used herein means an "examined Japanese patent publication"), optionally together with low-boiling organic solvents having boiling point of 50 to 160° C. These high-boiling organic solvents may be used as a mixture of two or more thereof.

The high-boiling organic solvent can be used in an amount 0 to 2.0 times, preferably 0 to 1.0 times, by mass as much as the dye-forming components as described above. In case where the recording layer contains the dye-forming components together with a binder, it is preferable that the amount of the high-boiling organic solvent is not more than 1 ml, still preferably not more than 0.5 ml and the most desirably not more than 0.3 ml, per gram of the binder.

The dye-forming components can be incorporated into the recording layer by using the polymer dispersion method as reported in JP-B-51-39, 853 and JP-B-51-59, 943, or the method of adding in the form of a dispersion of fine particles as reported in JP—A-62-30, 342.

In case where one of these dye-forming components is a compound substantially insoluble in water, it can be incorporated into the recording layer in the form of a dispersion of fine particles in the binder.

In case where the dye-forming components are hydrophobic compounds, these components can be incorporated into the recording layer in the form of a dispersion in a hydrophilic colloid. To disperse the dye-forming components in a hydrophilic colloid, use can be made of various surfactants, for example, the surfactants described in JP—A-59-157,636, pages 37–38 and the surfactants described in Research Disclosure as cited above.

Regarding the latex dispersion method falling within the category of the polymer dispersion method, the procedure, effects and examples of the latex for impregnation are reported in U.S. Pat. No. 4,199,363, West Germany Patent Application (OLS) U.S. Pat. No. 2,541,274, ibid. U.S. Pat. No. 2,541,230 and JP-B-53-41090, which are applicable in the invention. The dispersion method with the use of a polymer soluble in organic solvents is described in PCT WO88/00723, which is also applicable in the invention.

It is favorable that the polymerizable compound and the polymerization initiator as described above are contained in the recording layer in a state of emulsified/dispersed as oil droplets. These oil droplets may contain two or more polymerizable compounds.

The recording layer may further contain other additives, in addition to the dye-forming components, the polymerizable compound and the polymerization initiator. Examples of the additives include anti-staining agents described in JP-A-07-104448 (column 39, line 50 to column 70, line 9), JP-A-07-77775 (column 61, line 50 to column 62, line 49) and JP-A-07-301895 (column 87, line 49 to column 88, line 48); UV absorbers described in JP-A-62-215272 (p. 125, right upper column, line 2 to p. 127, left lower column, the final line), JP-A-2-33144 (p. 37, right lower column, line 14 to p. 38, left upper column, line 11) and European Patent 0,355,600A2 (p. 85, lines 22 to 31); and anti-fading agents described in JP-A-07-104448 (column 70, line 10 to column 71, line 2) As the anti-fading agents, compounds represented by the following general formula (XI) or (XII) are particularly preferable.

(XI)

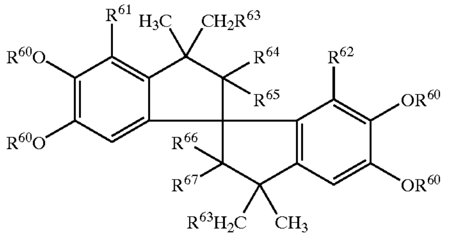

In general formula (XI), $R^{60}$ represents an alkyl group, an alkenyl group, an aryl group, an aralkyl group, a heterocyclic group, $R^{68}CO$—, $R^{69}SO_2$— or $R^{70}NHCO$— (wherein $R^{68}$ to $R^{70}$ represent each an alkyl group, an alkenyl group, an aryl group or a heterocyclic group). $R_{61}$ and $R^{62}$ represent each a hydrogen atom, a halogen atom, an alkyl group, an alkenyl group, an alkoxy group or an alkenoxy group. $R_{63}$ to $R^{67}$ represent each a hydrogen atom, an alkyl group, an alkenyl group or an aryl group.

(XII)

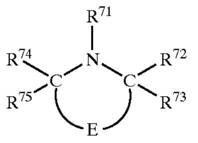

In general formula (XII), E represents a nonmetal atom needed in forming a 5- to 7-membered ring together with C and N.

In general formula (XII), $R^{71}$ represents a hydrogen atom, an alkyl group, an alkenyl group, an alkynyl group, an acyl group, a sulfonyl group, a sulfinyl group, an oxyradical group or a hydroxyl group.

In general formula (XII), $R^{72}R^{73}$, $R^{74}$ and $R^{75}$ represent each a hydrogen atom or an alkyl group.

It is preferable that the compound represented by general formula (XI) or (XII) is contained in an amount of from 5 to 200% by mol, still preferably from 50 to 100% by mol, based on the color developing agent oxidant precursor as described above.

As the substrate of the image-forming material according to the invention, use may be made of, for example, paper, coated paper, laminate paper, synthetic paper, films (for example, polyethylene terephthalate film, cellulose triacetate film, polyethylene film, polystyrene film, polycarbonate film), metal plates (for example, zinc plate, copper plate), and those obtained by subjecting these substrate to various treatments (for example, surface-treatment, undercoating, metallic vapor deposition). Moreover, reference may be made of the substrates described in Research Disclosure, vol. 200 (December, 1980), Item 20036 XVII. If necessary, the substrate may be provided with various layers appropriate for the purpose, for example, an anti-halation layer formed on the front face of the substrate and a slippage layer, an antistatic layer, an anti-curling layer and a pressure-sensitive adhesive layer formed on the back face of the substrate.

The image-forming material according to the invention is usable both in monochromatic image formation and color image formation. As an example of the constitution of a color image-forming material, citation may be made of an image-forming material having two or more recording layers (respectively containing polymerization initiators differing from each other in sensitive wavelength and dye-forming materials so combined as to give dyes of different color hues) laminated on a substrate. For example, an image-forming material for forming a full color image can be constructed by laminating 3 recording layers which are different from each other in sensitive wavelength and can develop respectively cyan, magenta and yellow colors.

In case where the image-forming material according to the invention has two or more recording layers, intermediate layer(s) may be provided between these recording layers. It is also possible to form a protective layer or a filter layer on the recording layer.

Regarding the light exposure source to be used in the latent image-forming step as described above, it is needless to say to select a light source appropriate for the sensitive wavelength of the photosensitive material contained in the recording layer. The light source may be selected further considering, for example, whether or not the image data are converted into electric signals, and the processing speed, compactness and electrical power consumption of the whole system. In case where the image data are once converted into electric signals and then recorded, use can be made, as the image exposure apparatus, of light emitting diodes and various lasers. Alternatively, it is also possible to employ various devices known as image display devices (for example, CRT, liquid crystal display, electroluminescence display, electrochromic display, plasma display). In such a case, the image data are available as image signals obtained from a video camera or an electron still camera, TV signals typified by Nippon Television Signal Committee (NTSC), image signals formed by dividing original images into a number of pixels with a scanner, or image signals recorded in various recording materials such as magnetic tapes and disks.

In the exposure of a color image, LEDs, lasers or fluorescent tubes may be appropriately combined and used depending on the color sensitivity of each recording layer. Either a combination of two or more light sources of the same type or a combination of those of different types is usable. In the field of photography, it has been a practice to employ red (R), green (G) and blue (B)-sensitivities as the color sensitivity of photosensitive materials. In recent years, however, attempts have been frequently made to use, for example, UV and IR in combination and thus the application range of light sources has been broadened. For example, photosensitive materials having color sensitivities of spectrum regions (G, R, IR), (R, IR (short wave), IR (long wave)), (UV (short wave), UV (medium wave), UV (long wave)) and (UV, B, G) are utilized. As the light source, it is also possible to use a combination of different types, for example, LEDs of two colors with laser. Regarding the light-emitting tubes or elements, a single tube or element may be used for each color followed by scanning exposure. Alternatively, use may be made of an array-type light source to elevate the exposure speed. Examples of the array usable include an LED array, a liquid crystal shutter array and a magneto-optical element shutter array. Moreover, use can be made of a light source constructed by combining a blue light-emitting diode, which has been rapidly advanced in recent years, with a green light-emitting diode or a red light-emitting diode.

The image display devices as described above include color display devices such as CRT and monochromatic display devices. A monochromatic display device may be exposed several times with the use of a combination of filters. An existing two-dimensional image display device may be converted into a one-dimensional device (for example, FOT) or a screen may be divided into several portions and combined with scanning.

As means of heating in the color developing step as described above, use can be made of various means. For example, the recording layer maybe heated by forming an exothermic layer on the surface of the substrate (in the side having no recording layer), as described in JP-A-61-294434. When the image-forming material according to the invention has this exothermic layer, it is favorable to cover the face of the substrate having the recording layer with, for example, a heat insulating material so as to prevent the evaporation of moisture or volatile components from the photosensitive material and to inhibit heat diffusion.

As the heating means, use may be made of a hot plate, an iron or a hot roller, as described in JP-A-61-147244. It is also possible that the photosensitive material is inserted between a hot roller and a belt and heated, as described in JP-A-62-144166.

EXAMPLES

The present invention will be described in greater detail with reference to the following Examples, but the invention should not be construed as being limited thereto.

Example 1

A composition of 10 mg of the color developing agent precursor (I-1), 10 mg of the coupler (A) and 0.5 ml of cumene was introduced into a test tube and heated in an oil bath at 150° C. for 30 minutes to thereby give a magenta dye.

Example 2

A composition of 10 mg of the color developing agent precursor (I-6), 10 mg of the coupler (B) and 0.5 ml of cumene was introduced into a test tube and heated in an oil bath at 150° C. for 30 minutes to thereby give a cyan dye.

Example 3

A composition of 10 mg of the color developing agent precursor (I-1), 10 mg of the coupler (A) and 30 mg of the activator (E-1) was introduced into a test tube and heated in an oil bath at 130° C. for 3 minutes to thereby give a magenta dye.

Example 4

A composition of 10 mg of the color developing agent precursor (I-6), 10 mg of the coupler (B) and 30 mg of the activator (E-1) was introduced into a test tube and heated in an oil bath at 130° C. for 3 minutes to thereby give a cyan dye.

$$Br—CH_2CO_2C_4H_8OCOCH{=}CH_2 \quad \text{(E-1)}$$

Example 5

10 mg of the color developing agent precursor (listed compound I-1), 10 mg of the coupler (A) shown below and 30 mg of the meso-ion complex (listed compound II-3) were introduced into a test tube and heated in an oil bath at 120° C. for 1 minute. Thus, a magenta dye was formed and the color hue of the liquid reaction mixture turned into magenta.

Example 6

10 mg of the color developing agent precursor (listed compound I-1), 10 mg of the coupler (B) shown below and 30 mg of the meso-ion complex (II-1) were introduced into a test tube and heated in an oil bath at 120° C. for 1 minute. Thus, a cyan dye was formed and the color hue of the liquid reaction mixture turned into cyan.

Coupler A

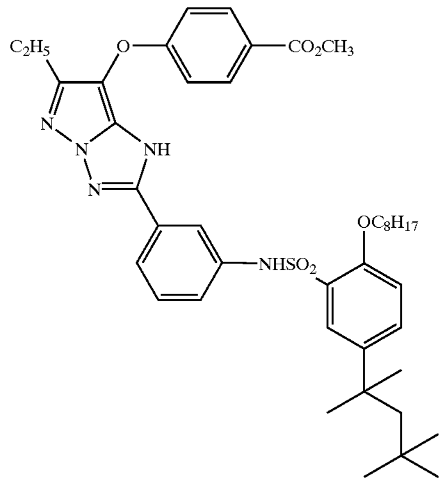

Coupler B

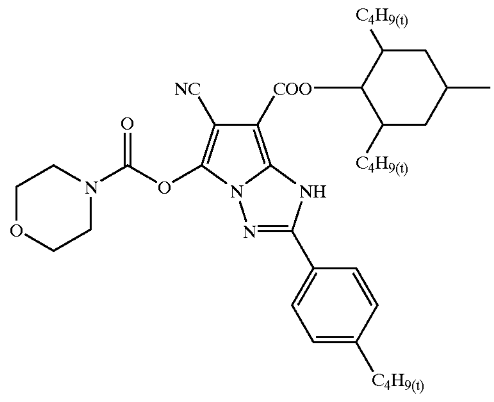

Example 7

0.25 g of the color developing agent precursor (I-1), 0.25 g of the coupler B as described above and 2.0 g of ethyl acetate were mixed and dissolved to give oil phase-1. Separately, 1.3 g of a 16% aqueous solution of gelatin, 0.034 g of a 5% aqueous solution of sodium dodecylbenzenesulfonate and 2.18 g of water were mixed together to give aqueous phase-1. After adding the aqueous phase-1 to the oil phase-1, the resultant mixture was emulsified and dispersed with a homogenizer. To the emulsion thus obtained was added 2.73 g of water. After mixing, the mixture was dry-coated on a polyethylene terephthalate film, having been under-coated with gelatin, at a coating dose of 17.5 cc/$m^2$ to thereby give a color developing agent precursor sheet.

On the other hand, 0.12 g of the activator (II-1), 0.36 g of a polymerizable monomer (trimethylolpropane triacrylate), 0.006 g of the following compound (BO-1), 0.003 g of the following compound (DY-1) and 0.3 g of ethyl acetate were mixed together and dissolved to give oil phase-2. Separately, 1.08 g of a 14% aqueous solution of gelatin, 0.26 g of a 5% aqueous solution of sodium dodecylbenzenesulfonate and 0.57 g of water were mixed together to give aqueous phase-2. After adding the aqueous phase-2 to the oil phase-2, the resultant mixture was emulsified and dispersed with a homogenizer. To the emulsion thus obtained was added 2 g of water. After mixing, the mixture was dry-coated on a polyethylene terephthalate film, having been under-coated with gelatin, at a coating dose of 21.5 cc/$m^2$ to thereby give an activator sheet.

polymerizable monomer underwent polymerization in the irradiated part of the activator sheet and thus the mobility of the activator was lowered, thereby forming the image.

Example 8

0.25 g of the color developing agent precursor (I-1), 0.25 g of the coupler B as described above and 2.0 g of ethyl acetate were mixed and dissolved to give oil phase-1. Separately, 1.3 g of a 16% aqueous solution of gelatin, 0.034 g of a 5% aqueous solution of sodium dodecylbenzenesulfonate and 2.18 g of water were mixed together to give aqueous phase-1. After adding the aqueous phase-1 to the oil phase-1, the resultant mixture was emulsified and dispersed with a homogenizer. To the emulsion thus obtained was added 2.73 g of water. After mixing, the mixture was dry-coated on a polyethylene terephthalate film, having been under-coated with gelatin, at a coating dose of 17.5 cc/$m^2$ to thereby give a color developing agent precursor sheet.

On the other hand, 0.3 g of the activator (E-1), 0.006 g of the compound (BO-1), 0.003 g of the compound (DY-1) and 0.3 g of ethyl acetate were mixed together and dissolved to give oil phase-2. Separately, 1.08 g of a 14% aqueous solution of gelatin, 0.26 g of a 5% aqueous solution of sodium dodecylbenzenesulfonate and 0.57g of water were mixed together to give aqueous phase-2. After adding the aqueous phase-2 to the oil phase-2, the resultant mixture was emulsified and dispersed with a homogenizer. To the emulsion thus obtained was added 2 g of water. After mixing, the mixture was dry-coated on a polyethylene terephthalate film, having been under-coated with gelatin, at a coating dose of 21.5 cc/$m^2$ to thereby give an electrophile sheet.

(BO-1)

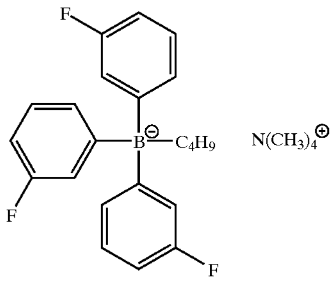

(DY-1)

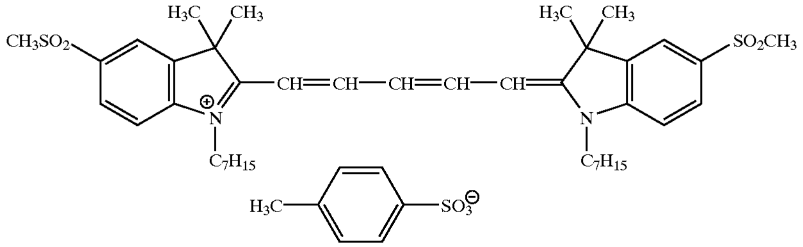

The activator sheet was exposed by using a halogen lamp (100,000 lux) for 10 seconds through a wedge having a transmission density of density level 0 to 4. Next, the activator sheet was adhered to the color developing agent precursor sheet in such a manner that the coated faces were brought into contact with each other and heated, from the back face of the activator sheet, at 130° C. for 10 seconds. When these sheets were separated from each other, a positive cyan image was obtained on the color developing agent precursor sheet. Namely, the part corresponding to the irradiated part of the activator sheet served as Dmin, while the part corresponding to the unirradiated part of the activator sheet served as Dmax. This is seemingly because the The electrophile sheet was exposed by using a halogen lamp (100,000 lux) for 10 seconds through a wedge having a transmission density of density level 0 to 4. Next, the electrophile sheet was adhered to the color developing agent precursor sheet in such a manner that the coated faces were brought into contact with each other and heated, from the back face of the electrophile sheet, at 130° C. for 10 seconds. When these sheets were separated from each other, a positive cyan image was obtained on the color developing agent precursor sheet. Namely, the part corresponding to the irradiated part of the electrophile sheet served as Dmin, while the part corresponding to the unirradiated part of the electrophile sheet served as Dmax. This is seemingly because the compound (E-1) underwent polymerization in the irradiated part of the electrophile sheet and thus the mobility was lowered, thereby forming the image.

Example 9

0.25 g of the metal salt meso-ion complex (listed compound II-3), 0.25 g of the coupler B as described above and 2.0 g of ethyl acetate were mixed and dissolved to give oil phase-1. Separately, 1.3 g of a 16% aqueous solution of gelatin, 0.034 g of a 5% aqueous solution of sodium dodecylbenzenesulfonate and 2.18 g of water were mixed together to give aqueous phase-1. After adding the aqueous phase-1 to the oil phase-1, the resultant mixture was emulsified and dispersed with a homogenizer. To the emulsion thus obtained was added 2.73 g of water. After mixing, the mixture was dry-coated on a polyethylene terephthalate film, having been under-coated with gelatin, at a coating dose of 17.5 $ml/m^2$ to thereby give sheet A.

On the other hand, 0.3 g of the color developing agent precursor (listed compound I-28), 0.20 g of a polymerizable compound (tirmethylolpropane triacrylate), 0.36 g of the compound (BO-1), 0.006 g of the compound (DY-1) and 0.3 g of ethyl acetate were mixed together and dissolved to give oil phase-2. Separately, 1.08 g of a 14% aqueous solution of gelatin, 0.26 g of a 5% aqueous solution of sodium dodecylbenzenesulfonate and 0.57 g of water were mixed together to give aqueous phase-2. After adding the aqueous phase-2 to the oil phase-2, the resultant mixture was emulsified and dispersed with a homogenizer. To the emulsion thus obtained was added 2 g of water. After mixing, the mixture was dry-coated on a polyethylene terephthalate film, having been under-coated with gelatin, at a coating dose of 21.5 $ml/m^2$ to thereby give sheet B.

The sheet B thus formed was exposed by using a halogen lamp (100,000 lux) for 10 seconds through a wedge having a transmission density of density level 0 to 4. Next, the sheet B was adhered to the sheet A in such a manner that the coated faces were brought into contact with each other and heated, from the back face of the sheet B, at 130° C. for 10 seconds. When these sheets were separated from each other, a positive cyan image was obtained on the sheet A. Namely, the part corresponding to the irradiated part of the sheet B served as Dmin, while the part corresponding to the unirradiated part of the sheet B served as Dmax. This is seemingly because, in the irradiated part of the sheet B, the polymerizable compound underwent polymerization and thus the mobility of the color developing agent precursor was lowered, which made the progress of the coupling reaction with the coupler impossible, thereby forming no dye; while, in the unirradiated part, the color developing agent precursor was converted into the oxidant under the action of the activator and thus underwent the coupling reaction with the coupler, thereby forming a dye.

The invention provides a dye-forming method whereby a dye can be economically and conveniently formed without resort to any oxidizing agents such as silver halides, color developing compositions and photosensitive materials by using the same. The invention further provides image-forming materials whereby images can be conveniently and economically formed without performing any liquid processing (in particular, image-forming materials for outputting digital image data), and an image-forming method.

While the present invention has been described in detail and with reference to specific examples thereof, it will be apparent to one skilled in the art that various changes and modifications can be made therein without departing from the spirit and scope thereof.

What is claimed is:

1. A compound represented by the following formula (VI):

(VI)

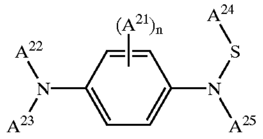

wherein $A^{21}$ represents a halogen atom, an alkyl group, an aryl group, a heterocyclic group, a carbonamido group, a sulfonamido group, an alkoxy group, an aryloxy group, an alkylthio group, an arylthio group, an amino group, a carbamoyl group, a sulfamoyl group, a cyano group, a sulfonyl group, an alkoxycarbonyl group, an aryloxycarbonyl group, an acyl group, a ureido group, a urethane group or an acyloxy group;

$A^{24}$ represents $C(=A^9)—A^{10}$, wherein $A^9$ represents $=O$, $=S$, $=N—A^{14}$ or $=C(A^{15})—C(A^{16})=N—A^{17}$, and wherein each of $A^{10}$ and $A^{14}$ to $A^{17}$ represents a halogen atom, an alkyl group, an aryl group, a heterocyclic group, a carbonamido group, a sulfonamido group, an alkoxy group, an aryloxy group, an alkylthio group, an arylthio group, an amino group, a carbamoyl group, a sulfamoyl group, a cyano group, a sulfonyl group, an alkoxycarbonyl group, an aryloxycarbonyl group, an acyl group, a ureido group, a urethane group or an acyloxy group;

n is an integer of from 0 to 4;

$A^{22}$ and $A^{23}$ represent each an alkyl group; and $A^{25}$ represents $—C(=O)—A^{26}$ or $—SO_2—A^{27}$ wherein $A^{26}$ represents $—NH—A^7$, and wherein $A^7$ represents a hydrogen atom, a halogen atom, an alkyl group, an aryl group, a heterocyclic group, a carbonamido group, a sulfonamido group, an alkoxy group, an aryloxy group, an alkylthio group, an arylthio group, an amino group, a carbamoyl group, a sulfamoyl group, a cyano group, a sulfonyl group, an alkoxycarbonyl group, an aryloxycarbonyl group, an acyl group, a ureido group, a urethane group or an acyloxy group; and wherein $A^{27}$ represents a hydrogen atom, an alkyl group, an aryl group, a heterocyclic group or an alkoxy group.

2. The compound according to claim 1, wherein $A^{24}$ is represented by formula (VII) and $A^{25}$ is represented by formula (VIII):

(VII)

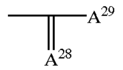

(VIII)

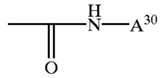

wherein $A^{28}$ represents $=O$, $=S$ or $=N—A^{31}$, wherein $A^{31}$ represents a halogen atom, an alkyl group, an aryl group, a heterocyclic group, a carbonamido group, a sulfonamido group, an alkoxy group, an aryloxy group, an alkylthio group, an arylthio group, an amino group, a carbamoyl group, a sulfamoyl group, a cyano group, a sulfonyl group, an alkoxycarbonyl group, an aryloxycarbonyl group, an acyl group, a ureido group, a urethane group or an acyloxy group;

$A^{29}$ represents a hydrogen atom, a halogen atom, an alkyl group, an aryl group, a heterocyclic group, a carbonamido group, a sulfonamido group, an alkoxy group, an aryloxy group, an alkylthio group, an arylthio group, an amino group, a carbamoyl group, a sulfamoyl group, a cyano group, a sulfonyl group, an alkoxycarbonyl group, an aryloxycarbonyl group, an acyl group, a ureido group, a urethane group or an acyloxy group; and $A^{30}$ represents a hydrogen atom, a halogen atom, an alkyl group, an aryl group, a heterocyclic group, a carbonamido group, a sulfonamido group, an alkoxy group, an aryloxy group, an alkylthio group, an arylthio group, an amino group, a carbamoyl group, a sulfamoyl group, a cyano group, a sulfonyl group, an alkoxycarbonyl group, an aryloxycarbonyl group, an acyl group, a ureido group, a urethane group or an acyloxy group.

* * * * *